United States Patent
Jiang et al.

(10) Patent No.: US 11,466,280 B2
(45) Date of Patent: *Oct. 11, 2022

(54) GENE TARGETING METHOD

(71) Applicant: HANGZHOU GENEKINE BIOTECH CO., LTD, Zhejiang (CN)

(72) Inventors: Youwei Jiang, Zhejiang (CN); Yunfei Li, Zhejiang (CN); Zhengwei Du, Zhejiang (CN); Huajun Liang, Zhejiang (CN)

(73) Assignee: HANGZHOU GENEKINE BIOTECH CO., LTD, Zhejiang (CN)

( * ) Notice: Subject to any disclaimer, the term of this patent is extended or adjusted under 35 U.S.C. 154(b) by 613 days.

This patent is subject to a terminal disclaimer.

(21) Appl. No.: 15/570,656

(22) PCT Filed: Apr. 29, 2016

(86) PCT No.: PCT/CN2016/080788
§ 371 (c)(1),
(2) Date: Oct. 30, 2017

(87) PCT Pub. No.: WO2016/173556
PCT Pub. Date: Nov. 3, 2016

(65) Prior Publication Data
US 2019/0093115 A1 Mar. 28, 2019

(30) Foreign Application Priority Data
Apr. 30, 2015 (CN) .......................... 201510218188.1

(51) Int. Cl.
*C12N 15/81* (2006.01)
*C12N 15/11* (2006.01)
*C12N 15/90* (2006.01)
*C12N 1/16* (2006.01)
*C12R 1/84* (2006.01)

(52) U.S. Cl.
CPC .............. *C12N 15/81* (2013.01); *C12N 15/11* (2013.01); *C12N 15/902* (2013.01); *C12N 15/905* (2013.01); *C12N 1/165* (2021.05); *C12R 2001/84* (2021.05)

(58) Field of Classification Search
None
See application file for complete search history.

(56) References Cited

U.S. PATENT DOCUMENTS 9,840,713 B2 * 12/2017 Zhang ..................... C12N 15/85

FOREIGN PATENT DOCUMENTS

| CN | 1498270 | 5/2004 |
| CN | 101679991 | 3/2010 |
| CN | 102120967 | 7/2011 |

OTHER PUBLICATIONS

Gardner et al., "Manipulating the Yeast Genome: Deletion, Mutation, and Tagging by PCR" 1205 Methods in Molecular Biology 45-78 (Year: 2014).*
Z. Chen et al., "Enhancement of the Gene Targeting Efficiency of Non-Conventional Yeasts by Increasing Genetic Redundancy," PLOS One, vol. 8, No. 3 (2013), 9 pages.
International Search Report for international appl. no. PCT/CN2016/080788, dated Aug. 4, 2016 (4 pages).
Buchholz, et al., "Depletion of Plasmodium berghei Plasmoredoxin Reveals a Non-Essential Role for Life Cycle Progression of the Malaria Parasite", PLOS ONE, vol. 3, No. 6, Jun. 25, 2008, p. e2474, 8 pages.
Gardner, et al., "Manipulating the Yeast Genome: Deletion, Mutation and Tagging by PCR", In: "Methods in Molecuar Biology", Jan. 1, 2014, 50 pages, Humana Press, Inc.
Extend European Search Report issued in European Application No. 16785984.2, dated Jan. 3, 2019, 7 pages.
Office Action issued in European Application No. 16785984.2, dated May 11, 2020, 5 pages.
Choi et al., "Use of combinatorial genetic libraries to humanize N-linked glycosylation in the yeast *Pichia pastoris*", PNAS, first published Apr. 29, 2003, vol. 100, No. 9, pp. 5022-5027, discussed in the specification.
Klinner et al., "Genetic aspects of targeted insertion mutagenesis in yeasts", FEMS Mircobiology Reviews, first published Oct. 24, 2003, pp. 201-223, discussed in the specification.
Kornfeld et al., "Assembly of Asparagine-Linked Oligosaccharides", Annual Reviews. Biochem, first published 1985, pp. 631-664, discussed in the specification.
Nett et al., "Cloning and disruption of the Pichia pastoris ARG1, ARG2, ARG3, HIS1, HIS2, HIS5, HIS6 genes and their use as auxotrophic markers", Wiley InterScience, first published 2005, pp. 295-304, discussed in the specification.
Spies et al., "3' UTR-isoform choice has limited influence on the stability and translational efficiency of most mRNAs in mouse fibroblasts", Genome Research, first published Sep. 26, 2013, pp. 2078-2090, discussed in the specification.
Paques et al., "Multiple Pathways of Recombination Induced by Double-Strand Breaks in *Saccharomyces cerevisiae*", Microbiology and Molecular Biology Reviews, first published Jun. 1999, pp. 349-404, discussed in the specification.
Payankaulam et al., "Transcriptional Repression: Conserved and Evolved Features", Current Biology, first published Sep. 14, 2010, pp. R764-R771, discussed in the specification.
Van Hoof et al., "Exosome-Mediated Recognition and Degradation of mRNAs Lacking a Termination Codon", Science Mag, vol. 295, Mar. 22, 2002, pp. 2262-2264 and 3 pages of supplementary web figures, discussed in the specification.

(Continued)

*Primary Examiner* — Nancy J Leith
(74) *Attorney, Agent, or Firm* — Hamre, Schumann, Mueller & Larson, P.C.

(57) ABSTRACT

A novel gene targeting method and a nucleotide construct for the method. The method integrates a nucleotide construct containing an interference gene in an effective gene targeting region independent of the gene by homologous recombination, thereby improving the targeting efficiency of the gene. The present invention also provides a gene targeting system for gene expression regulation and gene disruption.

17 Claims, 15 Drawing Sheets

Specification includes a Sequence Listing.

(56) References Cited

OTHER PUBLICATIONS

Wahls et al., "Meiotic Recombination Hotspots of Fission Yeast Are Directed to Loci that Express Non-Coding RNA", PLoS ONE, vol. 3, Issue 8, Aug. 6, 2008, pp. e2887, 8 pages provided, discussed in the specification.
Chen et al., "Enhancement of the Gene Targeting Efficiency of Non-Conventional Yeasts by Increasing Genetic Redundancy", PLoS ONE, vol. 8, Issue 3, Mar. 7, 2013, pp. e57952, 9 pages provided, discussed in the specification.
Examination Report issued in European Application No. 16785984. 2, dated Dec. 13, 2021; 5 pages provided.
Checketts Joshua A. et al.: "Homologous-Recombination Mediated Genome Editing at the Adesonine Deaminase Locus in Patient-Derived Fibroblasts Using TAL Effector Nucleases", Molecular Therapy—Nuclease Mediated Gene Targeting, vol. 20, suppl. 1, May 1, 2012; URL: https://www.cell.com/action/showPdf?pii=S1525-0016(16)36110-X.
Caroff N. et al.: "Mutations in the ampC promoter of *Escherichia coli* isolates resistant to oxyiminocephalosporins without extended spectrum beta-lactamase production", FEMS Microbiology Letters, vol. 173, accepted Feb. 22, 1999, pp. 459-465.

\* cited by examiner

SEQUENCE LISTING

```
<160> NUMBER OF SEQ ID NOS: 129

<210> SEQ ID NO 1
<211> LENGTH: 28
<212> TYPE: DNA
<213> ORGANISM: Artificial sequence
<220> FEATURE:
<221> NAME/KEY: misc_feature
<223> OTHER INFORMATION: primer
```

<400> SEQUENCE: 1
cggggtacct tctaagcgat cgtccgtc					28

<210> SEQ ID NO 2
<211> LENGTH: 36
<212> TYPE: DNA
<213> ORGANISM: Artificial sequence
<220> FEATURE:
<221> NAME/KEY: misc_feature
<223> OTHER INFORMATION: primer

<400> SEQUENCE: 2
cgcggatcca ggcctaacaa agtcaagaat aaaacg					36

<210> SEQ ID NO 3
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 3
gagaatgaat accttcctcg agcagttggt gagcttacat g					41

<210> SEQ ID NO 4
<211> LENGTH: 27
<212> TYPE: DNA
<213> ORGANISM: Artificial sequence
<220> FEATURE:
<221> NAME/KEY: misc_feature
<223> OTHER INFORMATION: primer

<400> SEQUENCE: 4
cggggtacca ctctgctgct ttttcag					27

<210> SEQ ID NO 5
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 5
acatgcatgc aggccttttc cccaacatat ttgg					34

<210> SEQ ID NO 6
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 6
catgtaagct caccaactgc tcgaggaagg tattcattct c					41

<210> SEQ ID NO 7
<211> LENGTH: 33
<212> TYPE: DNA
<213> ORGANISM: Artificial sequence
<220> FEATURE:
<221> NAME/KEY: misc_feature
<223> OTHER INFORMATION: primer

<400> SEQUENCE: 7
cgcgagctct cgaccaagag atgataactg tta                33

<210> SEQ ID NO 8
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 8
cggggtacca gctccaaggc aacaaattga ctac              34

<210> SEQ ID NO 9
<211> LENGTH: 28
<212> TYPE: DNA
<213> ORGANISM: Artificial sequence
<220> FEATURE:
<221> NAME/KEY: misc_feature
<223> OTHER INFORMATION: primer

<400> SEQUENCE: 9
cgggagctcg cttgaggaac ttttctgc                     28

<210> SEQ ID NO 10
<211> LENGTH: 30
<212> TYPE: DNA
<213> ORGANISM: Artificial sequence
<220> FEATURE:
<221> NAME/KEY: misc_feature
<223> OTHER INFORMATION: primer

<400> SEQUENCE: 10
ccgctcgagc agttggtgag cttacatgag                   30

<210> SEQ ID NO 11
<211> LENGTH: 38
<212> TYPE: DNA
<213> ORGANISM: Artificial sequence
<220> FEATURE:
<221> NAME/KEY: misc_feature
<223> OTHER INFORMATION: primer

<400> SEQUENCE: 11
acatgcatgc aggcctagaa caggaattat tggcttta          38

<210> SEQ ID NO 12
<211> LENGTH: 33
<212> TYPE: DNA
<213> ORGANISM: Artificial sequence
<220> FEATURE:
<221> NAME/KEY: misc_feature
<223> OTHER INFORMATION: primer

<400> SEQUENCE: 12
ccgctcgagg gctgatgata tttgctacga aca               33

<210> SEQ ID NO 13
<211> LENGTH: 36
<212> TYPE: DNA
<213> ORGANISM: Artificial sequence
<220> FEATURE:
<221> NAME/KEY: misc_feature
<223> OTHER INFORMATION: primer

<400> SEQUENCE: 13
cggggtacca tgqcgaaggc agatggcagt ttgctc         36

<210> SEQ ID NO 14
<211> LENGTH: 38
<212> TYPE: DNA
<213> ORGANISM: Artificial sequence
<220> FEATURE:
<221> NAME/KEY: misc_feature
<223> OTHER INFORMATION: primer

<400> SEQUENCE: 14
cgcggatcca ggcctcaata ccaatgacca acccagca         38

<210> SEQ ID NO 15
<211> LENGTH: 38
<212> TYPE: DNA
<213> ORGANISM: Artificial sequence
<220> FEATURE:
<221> NAME/KEY: misc_feature
<223> OTHER INFORMATION: primer

<400> SEQUENCE: 15
acatgcatgc aggcctggaa cattctctat cgctctcc         38

<210> SEQ ID NO 16
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 16
ccgctcgagc catgtcagca tacagtcctc cacg         34

<210> SEQ ID NO 17
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 17
cggggtacca cactatgtta ttaaaaccaa taga         34

<210> SEQ ID NO 18
<211> LENGTH: 39
<212> TYPE: DNA
<213> ORGANISM: Artificial sequence
<220> FEATURE:
<221> NAME/KEY: misc_feature
<223> OTHER INFORMATION: primer

<400> SEQUENCE: 18
cgcggatcca ggcctaaaaa ctatacagtc catgatatt         39

<210> SEQ ID NO 19
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 19
acatgcatgc aggcctttc cccaacatat ttgg         34

<210> SEQ ID NO 20
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 20
ccgctcgagc gtcgattaat ttgggggagc gcag                              34

<210> SEQ ID NO 21
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 21
cggggtacca tattcttatt cttccgatca ccag                              34

<210> SEQ ID NO 22
<211> LENGTH: 36
<212> TYPE: DNA
<213> ORGANISM: Artificial sequence
<220> FEATURE:
<221> NAME/KEY: misc_feature
<223> OTHER INFORMATION: primer

<400> SEQUENCE: 22
cgcggatcca ggcctaacaa agtcaagaat aaaacg                            36

<210> SEQ ID NO 23
<211> LENGTH: 46
<212> TYPE: DNA
<213> ORGANISM: Artificial sequence
<220> FEATURE:
<221> NAME/KEY: misc_feature
<223> OTHER INFORMATION: primer

<400> SEQUENCE: 23
catgtaagct caccaactgc tcgagggttc aaatctccag ctccac                 46

<210> SEQ ID NO 24
<211> LENGTH: 29
<212> TYPE: DNA
<213> ORGANISM: Artificial sequence
<220> FEATURE:
<221> NAME/KEY: misc_feature
<223> OTHER INFORMATION: primer

<400> SEQUENCE: 24
cggggtacca tcaccttgca tatattagg                                    29

<210> SEQ ID NO 25
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 25
ccgctcgagg tccttccaac ttccttcaaa tgta                              34

<210> SEQ ID NO 26
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 26
cggggtacct aaagaaagct agagtaaaat agat    34

<210> SEQ ID NO 27
<211> LENGTH: 42
<212> TYPE: DNA
<213> ORGANISM: Artificial sequence
<220> FEATURE:
<221> NAME/KEY: misc_feature
<223> OTHER INFORMATION: primer

<400> SEQUENCE: 27
catgtaagct caccaactgc tcgagttagt ccttccaact tc    42

<210> SEQ ID NO 28
<211> LENGTH: 29
<212> TYPE: DNA
<213> ORGANISM: Artificial sequence
<220> FEATURE:
<221> NAME/KEY: misc_feature
<223> OTHER INFORMATION: primer

<400> SEQUENCE: 28
cggggtacca gaaagctaga gtaaaatag    29

<210> SEQ ID NO 29
<211> LENGTH: 44
<212> TYPE: DNA
<213> ORGANISM: Artificial sequence
<220> FEATURE:
<221> NAME/KEY: misc_feature
<223> OTHER INFORMATION: primer

<400> SEQUENCE: 29
catgtaagct caccaactgc tcgagtttct tcatcggttc ttgc    44

<210> SEQ ID NO 30
<211> LENGTH: 29
<212> TYPE: DNA
<213> ORGANISM: Artificial sequence
<220> FEATURE:
<221> NAME/KEY: misc_feature
<223> OTHER INFORMATION: primer

<400> SEQUENCE: 30
cggggtacca aaacaacagt aacccaaac    29

<210> SEQ ID NO 31
<211> LENGTH: 32
<212> TYPE: DNA
<213> ORGANISM: Artificial sequence
<220> FEATURE:
<221> NAME/KEY: misc_feature
<223> OTHER INFORMATION: primer

<400> SEQUENCE: 31
acatgcatgc caaagactgc ttgtcgatga cc    32

<210> SEQ ID NO 32
<211> LENGTH: 32
<212> TYPE: DNA
<213> ORGANISM: Artificial sequence
<220> FEATURE:
<221> NAME/KEY: misc_feature
<223> OTHER INFORMATION: primer

<400> SEQUENCE: 32
ccgctcgagg aatgttccag gagagaattt gg                             32

<210> SEQ ID NO 33
<211> LENGTH: 32
<212> TYPE: DNA
<213> ORGANISM: Artificial sequence
<220> FEATURE:
<221> NAME/KEY: misc_feature
<223> OTHER INFORMATION: primer

<400> SEQUENCE: 33
cggggtacct ctatcgctct ccttccaagt tg                             32

<210> SEQ ID NO 34
<211> LENGTH: 30
<212> TYPE: DNA
<213> ORGANISM: Artificial sequence
<220> FEATURE:
<221> NAME/KEY: misc_feature
<223> OTHER INFORMATION: primer

<400> SEQUENCE: 34
cgcggatccc tattgatcaa atcttgagcc                                30

<210> SEQ ID NO 35
<211> LENGTH: 23
<212> TYPE: DNA
<213> ORGANISM: Artificial sequence
<220> FEATURE:
<221> NAME/KEY: misc_feature
<223> OTHER INFORMATION: primer

<400> SEQUENCE: 35
tgtttgtcca tttcataggc ttg                                       23

<210> SEQ ID NO 36
<211> LENGTH: 23
<212> TYPE: DNA
<213> ORGANISM: Artificial sequence
<220> FEATURE:
<221> NAME/KEY: misc_feature
<223> OTHER INFORMATION: primer

<400> SEQUENCE: 36
agaatgggct ctggtagcag gtg                                       23

<210> SEQ ID NO 37
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 37
ggagaagtaa tgagaagagc tggta                                     25

<210> SEQ ID NO 38

-continued

<210> SEQ ID NO 38
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 38
ttcattgaaa gtcagccacg attct                                  25

<210> SEQ ID NO 39
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 39
atattcagtt ccacaatttc cagtg                                  25

<210> SEQ ID NO 40
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 40
cagctccact gtggccaatc cctgg                                  25

<210> SEQ ID NO 41
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 41 ccgattttt caggtatttg attct                                   25

<210> SEQ ID NO 42
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 42
aatcccctgt caaaaacaac actcc                                  25

<210> SEQ ID NO 43
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 43
taaaaccaat agaatcgtgg ctgac                                  25

<210> SEQ ID NO 44
<211> LENGTH: 25

<212> TYPE: DNA
<213> ORGANISM: Artificial sequence
<220> FEATURE:
<221> NAME/KEY: misc_feature
<223> OTHER INFORMATION: primer

<400> SEQUENCE: 44
agatgaagga gtctctgtat attgg                                25

<210> SEQ ID NO 45
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 45
gtaaaaaaca atgctgggtt ggtca                                25

<210> SEQ ID NO 46
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 46
tcggaaagtg tcaatgggaa gagat                                25

<210> SEQ ID NO 47
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 47
aaaaacaatg ctgggttggt cattg                                25

<210> SEQ ID NO 48
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 48
aattcggaaa gtgtcaatgg gaaga                                25

<210> SEQ ID NO 49
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 49
aggaaaggat cgtggaagtg atgtg                                25

<210> SEQ ID NO 50
<211> LENGTH: 28
<212> TYPE: DNA

```
<213> ORGANISM: Artificial sequence
<220> FEATURE:
<221> NAME/KEY: misc_feature
<223> OTHER INFORMATION: primer

<400> SEQUENCE: 50
ctcctaacaa agtcaagaat aaaacgat                                    28

<210> SEQ ID NO 51
<211> LENGTH: 38
<212> TYPE: DNA
<213> ORGANISM: Artificial sequence
<220> FEATURE:
<221> NAME/KEY: misc_feature
<223> OTHER INFORMATION: primer

<400> SEQUENCE: 51
acatgcatgc aggcctggaa cattctctat cgctctcc                         38

<210> SEQ ID NO 52
<211> LENGTH: 28
<212> TYPE: DNA
<213> ORGANISM: Artificial sequence
<220> FEATURE:
<221> NAME/KEY: misc_feature
<223> OTHER INFORMATION: primer

<400> SEQUENCE: 52
caaaaacaaa tgaaagactt catgcgtc                                    28

<210> SEQ ID NO 53
<211> LENGTH: 28
<212> TYPE: DNA
<213> ORGANISM: Artificial sequence
<220> FEATURE:
<221> NAME/KEY: misc_feature
<223> OTHER INFORMATION: primer

<400> SEQUENCE: 53
gccccaatat actactctag gaaactcg                                    28

<210> SEQ ID NO 54
<211> LENGTH: 29
<212> TYPE: DNA
<213> ORGANISM: Artificial sequence
<220> FEATURE:
<221> NAME/KEY: misc_feature
<223> OTHER INFORMATION: primer

<400> SEQUENCE: 54
gattccaagt catcaaatac acctttcag                                   29

<210> SEQ ID NO 55
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 55
gttctcataa aatgactgtt c                                           21

<210> SEQ ID NO 56
<211> LENGTH: 40
<212> TYPE: DNA
<213> ORGANISM: Artificial sequence
```

<220> FEATURE:
<221> NAME/KEY: misc_feature
<223> OTHER INFORMATION: primer

<400> SEQUENCE: 56
gcagaaaagt tcctcaagca cttggaagga tacagcaaag                                40

<210> SEQ ID NO 57
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 57
ctttgctgta tccttccaag tgcttgagga acttttctgc                                40

<210> SEQ ID NO 58
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 58
cagtgttcac aatggacatc agttggtgag cttacatgag                                40

<210> SEQ ID NO 59
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 59
ctcatgtaag ctcaccaact gatgtccatt gtgaacactg                                40

<210> SEQ ID NO 60
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 60
gtcaaccaat ctctgagaaa c                                                    21

<210> SEQ ID NO 61
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 61
ctgaactttc accgccccaa tatac                                                25

<210> SEQ ID NO 62
<211> LENGTH: 39
<212> TYPE: DNA
<213> ORGANISM: Artificial sequence
<220> FEATURE:

<221> NAME/KEY: misc_feature
<223> OTHER INFORMATION: primer

<400> SEQUENCE: 62
gcagaaaagt tcctcaagca aacttcatct actagtacc            39

<210> SEQ ID NO 63
<211> LENGTH: 39
<212> TYPE: DNA
<213> ORGANISM: Artificial sequence
<220> FEATURE:
<221> NAME/KEY: misc_feature
<223> OTHER INFORMATION: primer

<400> SEQUENCE: 63
ggtactagta gatgaagttt gcttgaggaa cttttctgc            39

<210> SEQ ID NO 64
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 64
ctagaagaat ctggagttac agttggtgag cttacatgag           40

<210> SEQ ID NO 65
<211> LENGTH: 46
<212> TYPE: DNA
<213> ORGANISM: Artificial sequence
<220> FEATURE:
<221> NAME/KEY: misc_feature
<223> OTHER INFORMATION: primer

<400> SEQUENCE: 65
ctcatgtaag ctcaccaact gtaactccag attcttctag attttg    46

<210> SEQ ID NO 66
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 66
tgagcgattc aaactccttt g                              21

<210> SEQ ID NO 67
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 67
agacatttat gcagtcgatg ag                             22

<210> SEQ ID NO 68
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 68
gcagaaaagt tcctcaagct actcttgata gcaatttctg      40

<210> SEQ ID NO 69
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 69
cagaaattgc tatcaagagt agcttgagga acttttctgc      40

<210> SEQ ID NO 70
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 70
gcttcaatat actttcttc agttggtgag cttacatgag      40

<210> SEQ ID NO 71
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 71
ctcatgtaag ctcaccaact gaagaaaagt atattgaagc      40

<210> SEQ ID NO 72
<211> LENGTH: 24
<212> TYPE: DNA
<213> ORGANISM: Artificial sequence
<220> FEATURE:
<221> NAME/KEY: misc_feature
<223> OTHER INFORMATION: primer

<400> SEQUENCE: 72
cgttttcttg gtccagaatt tttg                       24

<210> SEQ ID NO 73
<211> LENGTH: 36
<212> TYPE: DNA
<213> ORGANISM: Artificial sequence
<220> FEATURE:
<221> NAME/KEY: misc_feature
<223> OTHER INFORMATION: primer

<400> SEQUENCE: 73
gcagaaaagt tcctcaagca gcccatttct tgccag          36

<210> SEQ ID NO 74
<211> LENGTH: 36
<212> TYPE: DNA
<213> ORGANISM: Artificial sequence
<220> FEATURE:
<221> NAME/KEY: misc_feature
<223> OTHER INFORMATION: primer

<400> SEQUENCE: 74
ctggcaagaa atgggctgct tgaggaactt ttctgc                                    36

<210> SEQ ID NO 75
<211> LENGTH: 42
<212> TYPE: DNA
<213> ORGANISM: Artificial sequence
<220> FEATURE:
<221> NAME/KEY: misc_feature
<223> OTHER INFORMATION: primer

<400> SEQUENCE: 75
gaggagggta ctaatcattc acagttggtg agcttacatg ag                             42

<210> SEQ ID NO 76
<211> LENGTH: 43
<212> TYPE: DNA
<213> ORGANISM: Artificial sequence
<220> FEATURE:
<221> NAME/KEY: misc_feature
<223> OTHER INFORMATION: primer

<400> SEQUENCE: 76
ctcatgtaag ctcaccaact gatgaatgat tagtaccctc ctc                            43

<210> SEQ ID NO 77
<211> LENGTH: 39
<212> TYPE: DNA
<213> ORGANISM: Artificial sequence
<220> FEATURE:
<221> NAME/KEY: misc_feature
<223> OTHER INFORMATION: primer

<400> SEQUENCE: 77
gcagaaaagt tcctcaagct caagcccatt tcttgccag                                 39

<210> SEQ ID NO 78
<211> LENGTH: 39
<212> TYPE: DNA
<213> ORGANISM: Artificial sequence
<220> FEATURE:
<221> NAME/KEY: misc_feature
<223> OTHER INFORMATION: primer

<400> SEQUENCE: 78
ctggcaagaa atgggcttga gcttgaggaa cttttctgc                                 39

<210> SEQ ID NO 79
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 79
gcgaggaggg tactaatcat cagttggtga gcttacatga g                              41

<210> SEQ ID NO 80
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 80
ctcatgtaag ctcaccaact gatgattagt accctcctcg c        41

<210> SEQ ID NO 81
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 81
caattagagg gacgatcctt g        21

<210> SEQ ID NO 82
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 82
gcagaaaagt tcctcaagcg agctccaagg caacaaattg        40

<210> SEQ ID NO 83
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 83
caatttgttg ccttggagct cgcttgagga acttttctgc        40

<210> SEQ ID NO 84
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 84
ccaaaagacc ccctgccaat cagttggtga gcttacatga g        41

<210> SEQ ID NO 85
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 85
ctcatgtaag ctcaccaact gattggcagg gggtcttttg g        41

<210> SEQ ID NO 86
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 86
gtctatggtt atgcaagcat tg                                           22

<210> SEQ ID NO 87
<211> LENGTH: 23
<212> TYPE: DNA
<213> ORGANISM: Artificial sequence
<220> FEATURE:
<221> NAME/KEY: misc_feature
<223> OTHER INFORMATION: primer

<400> SEQUENCE: 87
ttaaatatta cgcccaacga tcc                                          23

<210> SEQ ID NO 88
<211> LENGTH: 43
<212> TYPE: DNA
<213> ORGANISM: Artificial sequence
<220> FEATURE:
<221> NAME/KEY: misc_feature
<223> OTHER INFORMATION: primer

<400> SEQUENCE: 88
gcagaaaagt tcctcaagct taatactctt atactcttca aag                    43

<210> SEQ ID NO 89
<211> LENGTH: 43
<212> TYPE: DNA
<213> ORGANISM: Artificial sequence
<220> FEATURE:
<221> NAME/KEY: misc_feature
<223> OTHER INFORMATION: primer

<400> SEQUENCE: 89
ctttgaagag tataagagta ttaagcttga ggaactttc tgc                     43

<210> SEQ ID NO 90
<211> LENGTH: 44
<212> TYPE: DNA
<213> ORGANISM: Artificial sequence
<220> FEATURE:
<221> NAME/KEY: misc_feature
<223> OTHER INFORMATION: primer

<400> SEQUENCE: 90
gtgaaagttc agatgtttaa tgccagttgg tgagcttaca tgag                   44

<210> SEQ ID NO 91
<211> LENGTH: 44
<212> TYPE: DNA
<213> ORGANISM: Artificial sequence
<220> FEATURE:
<221> NAME/KEY: misc_feature
<223> OTHER INFORMATION: primer

<400> SEQUENCE: 91
ctcatgtaag ctcaccaact ggcattaaac atctgaactt tcac                   44

<210> SEQ ID NO 92
<211> LENGTH: 23
<212> TYPE: DNA
<213> ORGANISM: Artificial sequence
<220> FEATURE:
<221> NAME/KEY: misc_feature
<223> OTHER INFORMATION: primer

<400> SEQUENCE: 92
ctagtaccaa ttcattgttt tcg                                           23

<210> SEQ ID NO 93
<211> LENGTH: 23
<212> TYPE: DNA
<213> ORGANISM: Artificial sequence
<220> FEATURE:
<221> NAME/KEY: misc_feature
<223> OTHER INFORMATION: primer

<400> SEQUENCE: 93
ttaaatatta cgcccaacga tcc                                           23

<210> SEQ ID NO 94
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 94
tgagcgattc aaactccttt g                                             21

<210> SEQ ID NO 95
<211> LENGTH: 28
<212> TYPE: DNA
<213> ORGANISM: Artificial sequence
<220> FEATURE:
<221> NAME/KEY: misc_feature
<223> OTHER INFORMATION: primer

<400> SEQUENCE: 95
ccgctcgagg atgaggtaat tcttaggg                                      28

<210> SEQ ID NO 96
<211> LENGTH: 24
<212> TYPE: DNA
<213> ORGANISM: Artificial sequence
<220> FEATURE:
<221> NAME/KEY: misc_feature
<223> OTHER INFORMATION: primer

<400> SEQUENCE: 96
cgttttcttg gtccagaatt tttg                                          24

<210> SEQ ID NO 97
<211> LENGTH: 25
<212> TYPE: DNA
<213> ORGANISM: Artificial sequence
<220> FEATURE:
<221> NAME/KEY: misc_feature
<223> OTHER INFORMATION: primer

<400> SEQUENCE: 97
ctgaactttc accgccccaa tatac                                         25

<210> SEQ ID NO 98
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 98
gtctatggtt atgcaagcat tg                                            22

<210> SEQ ID NO 99
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 99
agacatttat gcagtcgatg ag                                    22

<210> SEQ ID NO 100
<211> LENGTH: 23
<212> TYPE: DNA
<213> ORGANISM: Artificial sequence
<220> FEATURE:
<221> NAME/KEY: misc_feature
<223> OTHER INFORMATION: primer

<400> SEQUENCE: 100
aagaagttcg tgagtagatg gtc                                   23

<210> SEQ ID NO 101
<211> LENGTH: 37
<212> TYPE: DNA
<213> ORGANISM: Artificial sequence
<220> FEATURE:
<221> NAME/KEY: misc_feature
<223> OTHER INFORMATION: primer

<400> SEQUENCE: 101
cgcggatccg ccaccatgac catgattacg gattcac                    37

<210> SEQ ID NO 102
<211> LENGTH: 46
<212> TYPE: DNA
<213> ORGANISM: Artificial sequence
<220> FEATURE:
<221> NAME/KEY: misc_feature
<223> OTHER INFORMATION: primer

<400> SEQUENCE: 102
ataagaatgc ggccgcctcg agttattttt gacaccagac caactg          46

<210> SEQ ID NO 103
<211> LENGTH: 44
<212> TYPE: DNA
<213> ORGANISM: Artificial sequence
<220> FEATURE:
<221> NAME/KEY: misc_feature
<223> OTHER INFORMATION: primer

<400> SEQUENCE: 103
ataagaatgc ggccgcctcg agtttttgac accagaccaa ctgg            44

<210> SEQ ID NO 104
<211> LENGTH: 30
<212> TYPE: DNA
<213> ORGANISM: Artificial sequence
<220> FEATURE:
<221> NAME/KEY: misc_feature
<223> OTHER INFORMATION: primer

<400> SEQUENCE: 104
cgcggatccg cttgaggaac ttttctgcac                            30

```
<210> SEQ ID NO 105
<211> LENGTH: 30
<212> TYPE: DNA
<213> ORGANISM: Artificial sequence
<220> FEATURE:
<221> NAME/KEY: misc_feature
<223> OTHER INFORMATION: primer

<400> SEQUENCE: 105
cgcggatccc agttggtgag cttacatgag                                         30

<210> SEQ ID NO 106
<211> LENGTH: 37
<212> TYPE: DNA
<213> ORGANISM: Artificial sequence
<220> FEATURE:
<221> NAME/KEY: misc_feature
<223> OTHER INFORMATION: primer

<400> SEQUENCE: 106
ataagaatgc ggccgcgctt gaggaacttt tctgcac                                 37

<210> SEQ ID NO 107
<211> LENGTH: 37
<212> TYPE: DNA
<213> ORGANISM: Artificial sequence
<220> FEATURE:
<221> NAME/KEY: misc_feature
<223> OTHER INFORMATION: primer

<400> SEQUENCE: 107
ataagaatgc ggccgccagt tggtgagctt acatgag                                 37

<210> SEQ ID NO 108
<211> LENGTH: 35
<212> TYPE: DNA
<213> ORGANISM: Artificial sequence
<220> FEATURE:
<221> NAME/KEY: misc_feature
<223> OTHER INFORMATION: primer

<400> SEQUENCE: 108
cgcggatcca gaacaggaat tattggcttt atttg                                   35

<210> SEQ ID NO 109
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 109
gaatccgtaa tcatggtcat ggctgatgat atttgctacg                              40

<210> SEQ ID NO 110
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 110
cgtagcaaat atcatcagcc atgaccatga ttacggattc                              40
```

-continued

```
<210> SEQ ID NO 111
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 111
ccgctcgagt tatttttgac accagaccaa ctgg                              34

<210> SEQ ID NO 112
<211> LENGTH: 34
<212> TYPE: DNA
<213> ORGANISM: Artificial sequence
<220> FEATURE:
<221> NAME/KEY: misc_feature
<223> OTHER INFORMATION: primer

<400> SEQUENCE: 112
ccgctcgaga gaaagctaga gtaaaataga tata                              34

<210> SEQ ID NO 113
<211> LENGTH: 29
<212> TYPE: DNA
<213> ORGANISM: Artificial sequence
<220> FEATURE:
<221> NAME/KEY: misc_feature
<223> OTHER INFORMATION: primer

<400> SEQUENCE: 113
cgcgagctca acaaagtcaa gaataaaac                                    29

<210> SEQ ID NO 114
<211> LENGTH: 44
<212> TYPE: DNA
<213> ORGANISM: Artificial sequence
<220> FEATURE:
<221> NAME/KEY: misc_feature
<223> OTHER INFORMATION: primer

<400> SEQUENCE: 114
tgtgcagaaa agttcctcaa gcggctgatg atatttgcta cgaa                   44

<210> SEQ ID NO 115
<211> LENGTH: 44
<212> TYPE: DNA
<213> ORGANISM: Artificial sequence
<220> FEATURE:
<221> NAME/KEY: misc_feature
<223> OTHER INFORMATION: primer

<400> SEQUENCE: 115
ttcgtagcaa atatcatcag ccgcttgagg aacttttctg caca                   44

<210> SEQ ID NO 116
<211> LENGTH: 45
<212> TYPE: DNA
<213> ORGANISM: Artificial sequence
<220> FEATURE:
<221> NAME/KEY: misc_feature
<223> OTHER INFORMATION: primer

<400> SEQUENCE: 116
ccgctcgaga catgcatgcc agttggtgag cttacatgag aagtc                  45

<210> SEQ ID NO 117
```

<211> LENGTH: 36
<212> TYPE: DNA
<213> ORGANISM: Artificial sequence
<220> FEATURE:
<221> NAME/KEY: misc_feature
<223> OTHER INFORMATION: primer

<400> SEQUENCE: 117
acatgcatgc atgaccatga ttacggattc actggc        36

<210> SEQ ID NO 118
<211> LENGTH: 20
<212> TYPE: DNA
<213> ORGANISM: Artificial sequence
<220> FEATURE:
<221> NAME/KEY: misc_feature
<223> OTHER INFORMATION: primer

<400> SEQUENCE: 118
gcttcgtctg ggactgggtg        20

<210> SEQ ID NO 119
<211> LENGTH: 20
<212> TYPE: DNA
<213> ORGANISM: Artificial sequence
<220> FEATURE:
<221> NAME/KEY: misc_feature
<223> OTHER INFORMATION: primer

<400> SEQUENCE: 119
aactgctgct ggtgttttgc        20

<210> SEQ ID NO 120
<211> LENGTH: 20
<212> TYPE: DNA
<213> ORGANISM: Artificial sequence
<220> FEATURE:
<221> NAME/KEY: misc_feature
<223> OTHER INFORMATION: primer

<400> SEQUENCE: 120
ctccttccac cgcccgttac        20

<210> SEQ ID NO 121
<211> LENGTH: 19
<212> TYPE: DNA
<213> ORGANISM: Artificial sequence
<220> FEATURE:
<221> NAME/KEY: misc_feature
<223> OTHER INFORMATION: primer

<400> SEQUENCE: 121
atgcgtccgc ccgctatta        19

<210> SEQ ID NO 122
<211> LENGTH: 20
<212> TYPE: DNA
<213> ORGANISM: Artificial sequence
<220> FEATURE:
<221> NAME/KEY: misc_feature
<223> OTHER INFORMATION: primer

<400> SEQUENCE: 122
gtgatgtgat ggactggacg        20

<210> SEQ ID NO 123
<211> LENGTH: 20

```
<212> TYPE: DNA
<213> ORGANISM: Artificial sequence
<220> FEATURE:
<221> NAME/KEY: misc_feature
<223> OTHER INFORMATION: primer

<400> SEQUENCE: 123
taaggcattg taatacgctg                                                  20

<210> SEQ ID NO 124
<211> LENGTH: 47
<212> TYPE: DNA
<213> ORGANISM: Artificial sequence
<220> FEATURE:
<221> NAME/KEY: misc_feature
<223> OTHER INFORMATION: primer

<400> SEQUENCE: 124
ccgctcgaga aaagagaggc tgaagctttg ccagtcaaca ccagatg                    47

<210> SEQ ID NO 125
<211> LENGTH: 28
<212> TYPE: DNA
<213> ORGANISM: Artificial sequence
<220> FEATURE:
<221> NAME/KEY: misc_feature
<223> OTHER INFORMATION: primer

<400> SEQUENCE: 125
ataagaatgc ggccgcttag tgatggtg                                         28

<210> SEQ ID NO 126
<211> LENGTH: 3669
<212> TYPE: DNA
<213> ORGANISM: P. pastoris

<400> SEQUENCE: 126
tgagccggcc agtaaccgtc ttggagctgt tcataagag tcattaggga tcaataacgt        60
tctaatctgt tcataacata caaatttat ggctgcatag ggaaaaattc tcaacagggt       120
agccgaatga ccctgatata gacctgcgac accatcatac ccatagatct gcctgacagc     180
cttaaagagc ccgctaaaag acccggaaaa ccgagagaac tctggattag cagtctgaaa     240
aagaatcttc actctgtcta gtggagcaat taatgtctta gcggcacttc ctgctactcc     300
gccagctact cctgaataga tcacatactg caaagactgc ttgtcgatga ccttggggtt     360
atttagcttc aagggcaatt tttgggacat tttggacaca ggagactcag aaacagacac     420
agagcgttct gagtcctggt gctcctgacg taggcctaga acaggaatta ttggctttat     480
ttgtttgtcc atttcatagg cttggggtaa tagatagatg acagagaaat agagaagacc     540
taatattttt tgttcatggc aaatcgcggg ttcgcggtcg ggtcacacac ggagaagtaa     600
tgagaagagc tggtaatctg gggtaaaagg gttcaaaaga aggtcgcctg tagggatgc     660 aatacaaggt tgtcttggag tttacattga ccagatgatt tggcttttc tctgttcaat     720 tcacattttt cagcgagaat cggattgacg gagaaatggc ggggtgtggg gtggatagat     780
ggcagaaatg ctcgcaatca ccgcgaaaga aagactttat ggaatagaac tactgggtgg     840
tgtaaggatt acatagctag tccaatggag tccgttggaa aggtaagaag aagctaaaac     900
cggctaagta actagggaag aatgatcaga ctttgatttg atgaggtctg aaaatactct     960
gctgcttttt cagttgcttt ttccctgcaa cctatcattt ccttttcat aagcctgcct    1020 tttctgtttt cacttatatg agttccgccg agacttcccc aaattctctc ctggaacatt    1080
```

```
ctctatcgct ctccttccaa gttgcgcccc ctggcactgc ctagtaatat taccacgcga   1140
cttatattca gttccacaat ttccagtgtt cgtagcaaat atcatcagcc atggcgaagg   1200
cagatggcag tttgctctac tataatcctc acaatccacc cagaaggtat tacttctaca   1260
tggctatatt cgccgtttct gtcatttgcg ttttgtacgg accctcacaa caattatcat   1320
ctccaaaaat agactatgat ccattgacgc tccgatcact tgatttgaag actttggaag   1380
ctccttcaca gttgagtcca ggcaccgtag aagataatct tcgaagacaa ttggagtttc   1440
attttcctta ccgcagttac gaaccttttc cccaacatat ttggcaaacg tggaaagttt   1500
ctccctctga tagttccttt ccgaaaaact tcaaagactt aggtgaaagt tggctgcaaa   1560
ggtccccaaa ttatgatcat tttgtgatac ccgatgatgc agcatgggaa cttattcacc   1620
atgaatacga acgtgtacca gaagtcttgg aagctttcca cctgctacca gagcccattc   1680
taaaggccga ttttttcagg tatttgattc ttttgcccg tggaggactg tatgctgaca    1740
tggacactat gttattaaaa ccaatagaat cgtggctgac tttcaatgaa actattggtg   1800
gagtaaaaaa caatgctggg ttggtcattg gtattgaggc tgatcctgat agacctgatt   1860
ggcacgactg gtatgctaga aggatacaat tttgccaatg gcaattcag tccaaacgag    1920
gacacccagc actgcgtgaa ctgattgtaa gagttgtcag cacgacttta cggaaagaga   1980
aaagcggtta cttgaacatg gtggaaggaa aggatcgtgg aagtgatgtg atggactgga   2040
cgggtccagg aatatttaca gacactctat ttgattatat gactaatgtc aatacaacag   2100
gccactcagg ccaaggaatt ggagctggct cagcgtatta caatgcctta tcgttggaag   2160
aacgtgatgc cctctctgcc cgcccgaacg gagagatgtt aaaagagaaa gtcccaggta   2220
aatatgcaca gcaggttgtt ttatgggaac aatttaccaa cctgcgctcc cccaaattaa   2280
tcgacgatat tcttattctt ccgatcacca gcttcagtcc agggattggc acagtggag    2340
ctggagattt gaaccatcac cttgcatata ttaggcatac atttgaagga agttggaagg   2400
actaaagaaa gctagagtaa aatagatata gcgagattag agaatgaata ccttcttcta   2460
agcgatcgtc cgtcatcata gaatatcatg gactgtatag ttttttttt gtacatataa    2520
tgattaaacg gtcatccaac atctcgttga cagatctctc agtacgcgaa atccctgact   2580
atcaaagcaa gaaccgatga agaaaaaaac aacagtaacc caaacaccac aacaaacact   2640
ttatcttctc ccccccaaca ccaatcatca agagatgtc ggaaccaaac accaagaagc    2700
aaaaactaac cccatataaa acatcctgg tagataatgc tggtaacccg ctctccttcc    2760
atattctggg ctacttcacg aagtctgacc ggtctcagtt gatcaacatg atcctcgaaa   2820
tgggtggcaa gatcgttcca gacctgcctc ctctggtaga tggagtgttg ttttgacag    2880
gggattacaa gtctattgat gaagataccc taaagcaact gggggacgtt ccaatataca   2940
gagactcctt catctaccag tgttttgtgc acaagacatc tcttcccatt gacactttcc   3000
gaattgacaa gaacgtcgac ttggctcaag atttgatcaa tagggccctt caagagtctg   3060
tggatcatgt cacttctgcc agcacagctg cagctgctgc tgttgttgtc gctaccaacg   3120
gcctgtcttc taaaccagac gctcgtacta gcaaaataca gttcactccc gaagaagatc   3180
gttttattct tgactttgtt aggagaaatc ctaaacgaag aaacacacat caactgtaca   3240
ctgagctcgc tcagcacatg aaaaaccata cgaatcattc tatccgccac agatttcgtc   3300
gtaatctttc cgctcaactt gattgggttt atgatatcga tccattgacc aaccaacctc   3360
gaaaagatga aaacgggaac tacatcaagg tacaagatct tccacaagga attcgtggtc   3420
```

| | |
|---|---|
| attattctgc ccaagatgat tacaatttgt gtttatcggt tcaacctttc attgaatctg | 3480 |
| tagatgagac aacaggccaa gaattttttca aacctctgaa aggtgtattt gatgacttgg | 3540 |
| aatctcgctt tcctcaccat acaaagactt cctggagaga cagattcaga aagtttgcct | 3600 |
| ctaaatacgg tgttcgtcag tacatcgcgt attatgaaaa gactgttgaa ctcaatggtg | 3660 |
| ttcctaatc | 3669 |

<210> SEQ ID NO 127
<211> LENGTH: 2811
<212> TYPE: DNA
<213> ORGANISM: P. pastoris

<400> SEQUENCE: 127

| | |
|---|---|
| ttaaatatta cgcccaacga tccaaacaac aatagaaacc atctgttgaa gtttctagct | 60 |
| gcctttatgg tgacttttag tattcctgtt gtgtcgttct cataaaatga ctgttctaca | 120 |
| gtcgataata agccactcat cttccacaac ttcaactgca cttcctccaa tgcaactaga | 180 |
| tcatgctttt caagctgctt gagattgatc ttcagtaatt ctttaacttc atcgtgtgat | 240 |
| gtgagcaaga cgagtaaata cttgagtttt gtcaagttat tactgccctt gtttgacatg | 300 |
| gattgctgta tttgagaaga aaatgaacg taaacttgaa tctccccagg tgaacttggc | 360 |
| gtgtatctta tctaccccag ctctaaagtt tacccgatga ggtaattctt agggataatt | 420 |
| tggtgtatgg atttgactaa attgccggag ttgattcaat gacagagaag cttacatgca | 480 |
| aggaacatga ttcgttgatc aacattagat gggtggcatg gagacgggtg ctatcgtttt | 540 |
| gtgcaatttg gtttgctgga gagtcgacca agagatgata actgttacta gcttctccg | 600 |
| taattagtgg tattttgtaa cttttaccaa taatcgttta tgaatacgga tattttcga | 660 |
| ccttatccag tgccaaatca cgtaacttaa tcatggttta aatactccac ttgaacgatt | 720 |
| cattattcag aaaaaagtca ggttggcaga acactggg cgctttgaag agtataagag | 780 |
| tattaagcat taaacatctg aacttttcacc gccccaatat actactctag gaaactcgaa | 840 |
| aaattccttt ccatgtgtca tcgcttccaa cacactttgc tgtatccttc caagtatgtc | 900 |
| cattgtgaac actgatctgg acggaatcct accttttaatc gccaaaggaa aggttagaga | 960 |
| catttatgca gtcgatgaga acaacttgct gttcgtcgca actgaccgta tctccgctta | 1020 |
| cgatgtgatt atgacaaacg gtattcctga taagggaaag atttttgactc agctctcagt | 1080 |
| tttctggttt gattttttgg caccctacat aaagaatcat ttggttgctt ctaatgacaa | 1140 |
| ggaagtcttt gctttactac catcaaaact gtctgaagaa aaatacaaat ctcaattaga | 1200 |
| gggacgatcc ttgatagtaa aaaagcacag actgatacct ttggaagcca ttgtcagagg | 1260 |
| ttacatcact ggaagtgcat ggaaagagta caagaactca aaaactgtcc atggagtcaa | 1320 |
| ggttgaaaac gagaaccttc aagagagcga cgcctttcca actccgattt tcacaccttc | 1380 |
| aacgaaagct gaacagggtg aacacgatga aacatctct attgaacaag ctgctgagat | 1440 |
| tgtaggtaaa gacatttgtg agaaggtcgc tgtcaaggcg gtcgagttgt attctgctgc | 1500 |
| aaaaaacttc gcccttttga gggggatcat tattgctgat acgaaattcg aatttggact | 1560 |
| ggacgaaaac aatgaattgg tactagtaga tgaagttta actccagatt cttctagatt | 1620 |
| ttggaatcaa aagacttacc aagtgggtaa atcgcaagag agttacgata gcagtttct | 1680 |
| cagagattgg ttgacggcca acggattgaa tggcaaagag ggcgtagcca tggatgcaga | 1740 |
| aattgctatc aagagtaaag aaaagtatat tgaagcttat gaagcaatta ctggcaagaa | 1800 |
| atgggcttga atgattagta ccctcctcgc cttttttcaga catctgaaat ttcccttatt | 1860 |

```
cttccaattc catataaaat cctatttagg taattagtaa acaatgatca taaagtgaaa    1920
tcattcaagt aaccattccg tttatcgttg atttaaaatc ataacgaat gaatgtcggt     1980 ctgagtagtc aatttgttgc cttggagctc attggcaggg ggtcttttgg ctcagtatgg    2040
aaggttgaaa ggaaaacaga tggaaagtgg ttcgtcagaa aagaggtatc ctacatgaag    2100
atgaatgcca aagagatatc tcaagtgata gctgagttca gaattcttag tgagttaagc    2160
catcccaaca ttgtgaagta ccttcatcac gaacatattt ctgagaataa aactgtcaat    2220
ttatacatgg aatactgtga tggtggagat ctctccaagc tgattcgaac acatagaagg    2280
aacaaagagt acatttcaga agaaaaaata tggagtattt ttacgcaggt tttattagca    2340
ttgtatcgtt gtcattatgg aactgatttc acggcttcaa aggagtttga atcgctcaat    2400
aaaggtaata gacgaaccca gaatccttcg tgggtagact cgacaagagt tattattcac    2460
agggatataa aacccgacaa catctttctg atgaacaatt caaaccttgt caaactggga    2520
gattttggat tagcaaaaat tctgaccaa gaaaacgatt tgccaaaac atacgtcggt      2580 acgccgtatt acatgtctcc tgaagtgctg ttggaccaac cctactcacc attatgtgat    2640
atatggtctc ttgggtgcgt catgtatgag ctatgtgcat tgaggcctcc ttttcaagcc    2700
actacacatt tacaattaca acaaaagatc caagaaggga cattccctcc acttccggac    2760
gtattttcac cccggttaag atctctgatc aatgcttgca taaccataga c             2811

<210> SEQ ID NO 128
<211> LENGTH: 3075
<212> TYPE: DNA
<213> ORGANISM: E. coli

<400> SEQUENCE: 128
atgaccatga ttacggattc actggccgtc gttttacaac gtcgtgactg ggaaaaccct     60
ggcgttaccc aacttaatcg ccttgcagca catccccctt tcgccagctg gcgtaatagc    120
gaagaggccc gcaccgatcg cccttcccaa cagttgcgca gcctgaatgg cgaatggcgc    180
tttgcctggt ttccggcacc agaagcggtg ccggaaagct ggctggagtg cgatcttcct    240
gaggccgata ctgtcgtcgt cccctcaaac tggcagatgc acggttacga tgcgcccatc    300
tacaccaacg tgacctatcc cattacggtc aatccgccgt ttgttcccac ggagaatccg    360
acgggttgtt actcgctcac atttaatgtt gatgaaagc ggctacagga aggccagacg    420
cgaattattt ttgatggcgt taactcggcg tttcatctgt ggtgcaacgg cgctgggtc     480 ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg gtggttatgc cgatcgcgtc acactacgtc tgaacgtcga aaacccgaaa    900
ctgtggagcg ccgaaatccc gaatctctat cgtgcggtgg ttgaactgca caccgccgac    960
ggcacgctga ttgaagcaga agcctgcgat gtcggtttcc gcgaggtgcg gattgaaaat   1020
ggtctgctgc tgctgaacgg caagccgttg ctgattcgag gcgttaaccg tcacgagcat   1080
catcctctgc atggtcaggt catggatgag cagacgatgg tgcaggatat cctgctgatg   1140
```

| | |
|---|---|
| aagcagaaca actttaacgc cgtgcgctgt tcgcattatc cgaaccatcc gctgtggtac | 1200 |
| acgctgtgcg accgctacgg cctgtatgtg gtggatgaag ccaatattga aacccacggc | 1260 |
| atggtgccaa tgaatcgtct gaccgatgat ccgcgctggc taccggcgat gagcgaacgc | 1320 |
| gtaacgcgaa tggtgcagcg cgatcgtaat cacccgagtg tgatcatctg gtcgctgggg | 1380 |
| aatgaatcag gccacggcgc taatcacgac gcgctgtatc gctggatcaa atctgtcgat | 1440 |
| ccttcccgcc cggtgcagta tgaaggcggc ggagccgaca ccacggccac cgatattatt | 1500 |
| tgcccgatgt acgcgcgcgt ggatgaagac cagcccttcc cggctgtgcc gaaatggtcc | 1560 |
| atcaaaaaat ggctttcgct acctggagag acgcgcccgc tgatcctttg cgaatacgcc | 1620 |
| cacgcgatgg gtaacagtct tggcggtttc gctaaatact ggcaggcgtt tcgtcagtat | 1680 |
| ccccgtttac agggcggctt cgtctggac tgggtggatc agtcgctgat taaatatgat | 1740 |
| gaaaacggca accgtggtc ggcttacggc ggtgattttg gcgatacgcc gaacgatcgc | 1800 |
| cagttctgta tgaacggtct ggtctttgcc gaccgcacgc cgcatccagc gctgacggaa | 1860 |
| gcaaaacacc agcagcagtt tttccagttc cgtttatccg gcaaaccat cgaagtgacc | 1920 |
| agcgaatacc tgttccgtca tagcgataac gagctcctgc actggatggt ggcgctggat | 1980 |
| ggtaagccgc tggcaagcgg tgaagtgcct ctggatgtcg ctccacaagg taaacagttg | 2040 |
| attgaactgc ctgaactacc gcagccggag agcgccgggc aactctggct cacagtacgc | 2100 |
| gtagtgcaac cgaacgcgac cgcatggtca gaagccggac acatcagcgc ctggcagcag | 2160 |
| tggcgtctgg ctgaaaacct cagcgtgaca ctccccgccg cgtcccacgc catcccgcat | 2220 |
| ctgaccacca gcgaaatgga ttttttgcatc gagctgggta ataagcgttg gcaatttaac | 2280 |
| cgccagtcag gctttctttc acagatgtgg attggcgata aaaacaact gctgacgccg | 2340 |
| ctgcgcgatc agttcacccg tgcaccgctg gataacgaca ttggcgtaag tgaagcgacc | 2400 |
| cgcattgacc ctaacgcctg ggtcgaacgc tggaaggcgg cgggccatta ccaggccgaa | 2460 |
| gcagcgttgt tgcagtgcac ggcagataca cttgctgatg cggtgctgat tacgaccgct | 2520 |
| cacgcgtggc agcatcaggg gaaaaaccta tttatcagcc ggaaaaccta ccggattgat | 2580 |
| ggtagtggtc aaatggcgat taccgttgat gttgaagtgg cgagcgatac accgcatccg | 2640 |
| gcgcggattg gcctgaactg ccagctggcg caggtagcag agcgggtaaa ctggctcgga | 2700 |
| ttagggccgc aagaaaacta tcccgaccgc cttactgccg cctgttttga ccgctgggat | 2760 |
| ctgccattgt cagacatgta tacccccgtac gtcttcccga gcgaaaacgg tctgcgctgc | 2820 |
| gggacgcgcg aattgaatta tggcccacac cagtggcgcg cgacttcca gttcaacatc | 2880 |
| agccgctaca gtcaacagca actgatggaa accagccatc gccatctgct gcacgcggaa | 2940 |
| gaaggcacat ggctgaatat cgacggtttc catatgggga ttggtggcga cgactcctgg | 3000 |
| agcccgtcag tatcggcgga attccagctg agcgccggtc gctaccatta ccagttggtc | 3060 |
| tggtgtcaaa aataa | 3075 |

<210> SEQ ID NO 129
<211> LENGTH: 459
<212> TYPE: DNA
<213> ORGANISM: Artificial sequence
<220> FEATURE:
<221> NAME/KEY: misc_feature
<223> OTHER INFORMATION: DNA sequence of mouse IL-22 mature peptide containing his-tag with optimized codon for yeast

<400> SEQUENCE: 129

| | |
|---|---|
| ttgccagtca acaccagatg caaattggag gtctcaaact ttcaacagcc atacatcgtt | 60 |

```
aatagaactt ttatgcttgc taaggaagct tcattggccg ataacaatac cgacgttaga    120
ttgattggtg aaaagctttt tagaggagtc agtgccaagg atcaatgtta cttgatgaaa    180
caggttttga acttcactct tgaagatgtc ttgcttccac aatcagacag atttcaacct    240
tatatgcagg aggttgtccc attcttgaca aagctttcaa atcagttgtc ttcctgccat    300
attagtggag atgaccaaaa catccagaag aatgttagaa gattgaaaga aactgtcaag    360
aaacttggtg aatctggaga gattaaagca atcggagagt tggacttgct ttttatgtcc    420
ttgagaaacg cttgtgttca tcaccatcac catcactaa                           459
```

GENE TARGETING METHOD

INCORPORATION BY REFERENCE OF MATERIAL IN ASCII TEXT FILE

This application incorporates by reference the Sequence Listing contained in the following ASCII text files filed on Sep. 4, 2018:

Filename: Sequence Listing, Sequence Name: U.S. Ser. No. 15/570,656, Version: 2, Sub-Version: 1, created Sep. 4, 2018, 38,905 bytes in size.

TECHNICAL FIELD

The present invention relates to the field of biotechnology; in particular, to a novel gene targeting method and to a nucleotide construct for using in the method.

BACKGROUND

In genome of an organism, each gene generally consists of coding region and regulatory regions. Coding region or open reading frame (ORF) encodes proteins and RNA chains with various biological functions. The boundary of a protein coding sequence includes a start codon at the 5' terminus (N-terminus) and a translation stop nonsense codon at the 3' terminus (C-terminus). The regulatory regions preceding (5' region) and following (3' region) the coding region contain regulatory DNA elements, such as promoter, enhancer, terminator, polyadenylation signal, 5' untranslated region (5' UTR), and 3' untranslated region (3' UTR), which control various aspects of a gene expression process, including transcription, translation, and RNA stability, etc.

In an organism, gene expression involves two major steps: firstly, encoded gene is transcribed from DNA to messenger RNA (mRNA) or RNA; and, secondly, mRNA is translated to protein. Expression of a gene can be controlled at both levels of transcription and translation, which are mediated by DNA elements in regulatory regions.

Transcription of a gene is initiated by the promoter, and extends to the terminator. A promoter is a specific region of a gene sequence that is recognized by RNA polymerase and is initially transcribed, which is a sequence that controls the initiation of transcription and determines the expression intensity of the gene. The terminator is a specific sequence in the gene sequence responsible for transcription termination, which provides a signal to trigger the transcription machine to release the newly synthesized mRNA (or RNA) to terminate the transcription.

Translation is a process in which mRNA molecule is used as a template to synthesize a protein. A mature mRNA composed of three parts, 5' UTR, ORF, and 3' UTR. 5' UTR is scanned by the translation initiation complex in a 5' to 3' direction until an initiator AUG codon is encountered. At this position, ribosome moves from 5' terminus to 3' terminus along mRNA, and initiates synthesis of protein from N terminus to C terminus. As a stop codon (UAA, UAG or UGA) is encountered by ribosome, the protein synthesis is terminated and the protein is released from the ribosome.

In nature, methods and/or tools to predictably control the expression of any target gene would be beneficial for biological research and numerous biotechnology applications.

Gene targeting has been widely used to disrupt or enhance the activity of a gene. It is a process for chromosomal integration of the exogenous DNA at a genetic locus, which causes the gene at the target locus to be modified, replaced or duplicated. Gene targeting is a process common to all life and can be used for any gene, regardless of its transcriptional and translational activity.

Gene targeting is mediated via the repair of DNA double-strand breaks (DSBs). Such repair occurs via two distinctively different molecular mechanisms: homologous recombination (HR) pathway and non-homologous end-joining (NHEJ) pathway. In HR gene targeting, an exogenous DNA fragment, usually a selectable marker gene is precisely integrated at its homologous genome counter-part through homologous sequences at each end. On the contrary, in non-homologous end-joining pathway, an exogenous DNA fragment with selectable marker gene will randomly integrate at nonhomologous chromosomal sites. When the exogenous DNA fragment is transformed into cells, HR competes with NHEJ pathways (Paques and Haber 1999, Microbiology and Molecular Biology Reviews, 63: 349-404). Therefore, the efficiency of site-specific gene targeting is determined by the relative strength between HR and NHEJ pathways.

Although non-homologous end-joining pathway is attributed as a major factor for low efficiency of gene targeting, the efficiency of HR gene targeting in strains with the same genetic background can be locus dependent. The molecular mechanism for this locus dependent phenomenon is not well understood. One possible reason is that there are hotspot regions along each chromosome and homologous recombination is positioned preferentially at hotspots (Wahls et al. Plos One 3:e2887).

The efficiency of homologous recombination genes targeting in different biological systems is also significantly different. Conventional yeast, *Saccharomyces cerevisiae* and fission yeast, *Schizosaccharomyces pombe*, have very efficient HR gene targeting systems. However, the gene targeting efficiencies via homogenous recombination in methylotrophic yeast *Pichia pastoris* and other "non-conventional" yeasts, such as *Hansenula polymorpha, Yarrowia lipolytica, Pichia stipitis* and *Kluyveromyces lactis* can be extremely low. Most organisms, including fungi and eukaryotic organisms, have very low efficiencies in HR gene targeting (Klinner U, et al (2004) Fems Microbiology Reviews 28: 201-223; Gregg J M (2010) *Pichia* Protocols, Second edition. Totowa, N.J.: Humanna Press).

While it is well known that the efficiency of HR gene targeting can be dependent on competition between homologous recombination pathway and non-homologous end-joining pathway, and also dependent on genomic locus and organism system, little is know about HR targeting at different positions in coding and regulatory regions of a gene, especially in genes which are difficult for disruption.

Therefore, there is an urgent need in the art for a gene targeting method to improve the gene targeting efficiency, especially for a gene which is difficult for efficient disruption via conventional method.

SUMMARY OF THE INVENTION

The purpose of the present invention is to provide a gene targeting method to improve gene targeting efficiency, especially for a gene which is difficult for efficient disruption via conventional method, and material means used in the method.

In the first aspect, a nucleotide construct for regulating genes is provided in the present invention, with the following structures:

5'-A-B-C-3' wherein A is 5' homologous sequence, B is interfering gene, and C is a 3' homologous sequence;

the 5' homologous sequence and 3' homologous sequence allow the recombination site of the nucleotide construct to be located between the first nucleotide of the start codon of the gene to be regulated and the $110^{th}$, preferred $50^{th}$ nucleotide upstream from the first nucleotide of the start codon of the gene to be regulated, or the 5' and 3' homologous sequences allow the recombination site of the nucleotide construct to be located between the $100^{th}$, $50^{th}$ or $20^{th}$, preferred $50^{th}$ nucleotide upstream from the first nucleotide of the stop codon of the gene to be regulated and the $300^{th}$ nucleotide downstream from the first nucleotide of the stop codon of the gene to be regulated.

In a specific embodiment, the recombination sites are separated by 0-20 nucleotides; preferably 0-5 nucleotides; and most preferably 0 nucleotide.

In a preferred embodiment, there can be more than one interfering gene, and each interfering gene can be identical or different.

In a preferred embodiment, the interfering gene can be a marker gene.

In a preferred embodiment, the nucleotide construct can be in a circular or linear form.

In a specific embodiment, the gene to be regulated can be a gene, the recombination efficiency of which is low; preferably <3%; and most preferably <1%.

In a specific embodiment, the gene to be regulated is OCH1, ADE1 gene.

In a preferred embodiment, the length of the homologous sequence is 400-1200 bp (base pair), 500-1000 bp, 600-800 bp.

In the second aspect, a host cell comprising the nucleotide construct according to the first aspect of the present invention.

In a specific embodiment, the host cell is yeast cell.

In a preferred embodiment, the yeast is *Saccharomyces cerevisiae, Schizosaccharomyces pombe, Pichia pastoris, Hansenula polymorpha, Yarrowia lipolytica, Pichia stipitis* or *Kluyveromyces lactis*.

In a preferred embodiment, the yeast is *Pichia pastoris, Hansenula polymorpha, Yarrowia lipolytica, Pichia stipitis* or *Kluyveromyces lactis*.

In the third aspect, a method for regulating expression of a gene is provided in the present invention, comprising:
  a) constructing the nucleotide construct according to the first aspect of the present invention; and
  b) introducing the nucleotide construct constructed in step a) into a cell, thereby integrating the nucleotide construct into the gene to be regulated via homogeneous recombination.

In a specific embodiment, the gene to be regulated can be a gene, the recombination efficiency of which is low; preferably <3%; and most preferably <1%.

In a preferred embodiment, the gene to be regulated is OCH1, ADE1 gene.

In a preferred embodiment, the method can further comprise step c) testing the expression of the gene to be regulated in the cell obtained in step b).

In the fourth aspect, a method for engineering a strain is provided in the present invention, comprising:
  a) constructing the nucleotide construct according to the first aspect of the present invention; and
  b) introducing the nucleotide construct constructed in step a) into a strain to be engineered.

In a preferred embodiment, the method can further comprise step c) screening the engineered strain.

In the fifth aspect, use of the strain engineered by the method according to the fourth aspect of the present invention is provided, for producing recombinant proteins, metabolites and used in biocatalytic reaction.

In a preferred embodiment, the expression of OCH1 gene is inhibited and the glycosylation pattern in the recombinant protein is altered through HR integration upstream to encoding region of OCH1 in yeast.

In a preferred embodiment, the use for producing metabolites means increasing the yield of isobutanol through HR integration upstream to encoding region of LPD1 in yeast to inhibit the expression of LPD1 gene; and inhibit the metabolic competitive route; and facilitating efficient production of L-lactic acid through HR integration upstream to encoding region of PDC1 in yeast to inhibit the expression of PDC1 gene.

In a preferred embodiment, the use in bio-catalysis means enhancing biocatalytic ability of yeast and increasing the conversion efficiency of glucose to phenylethanol through HR integration upstream to encoding region of ARO8 in yeast and inhibiting the expression of ARO8 gene.

It should be understood that in the present invention, the technical features specifically mentioned above and below (such as in the Examples) can be combined with each other, thereby constituting a new or preferred technical solution which needs not be individually described.

give 1300, 2550, and 2550 bp bands with P1/P2 primer pair, respectively; lane 9, wild-type OCH1 in JC301 gives no band with P3/P4 primer pair; lane 10, 11, 12, gene integrations at three positions (−1/1), (1212/+1), and (+3/+4) give 3500, 2500, and 2300 bp bands with P3/P4 primer pair, respectively.

FIG. 5 depicts a scheme of integration at different positions in ADE1 locus (DNA sequence of Pichia pastoris PR-aminoimidazole succinyl carboxamide synthase (ADE1) is shown in SEQ ID NO: 127) in P. pastoris genome. Vector components are not drawn to scale. A. diagrams the integration positions of targeting cassette into the ADE1 locus of Pichia pastoris. The integration positions are indicated by arrows and labeled with nucleotide numbers. B. depicts the integration of targeting cassette into the ADE1 locus of P. pastoris by double cross-over homologous recombination (knock-in). The cross represents homologous recombination. C shows a result of PCR verification for integration at different positions in ADE1 locus. M, DNA size marker; lane 1-13, genomic DNAs from 13 random selected colonies were verified by PCR with P5/P6 primer pair. Wild-type ADE1 gives a 2398 bp band, and gene integration at the position (912/+1) gives a 3763 bp band.

Figure 6:
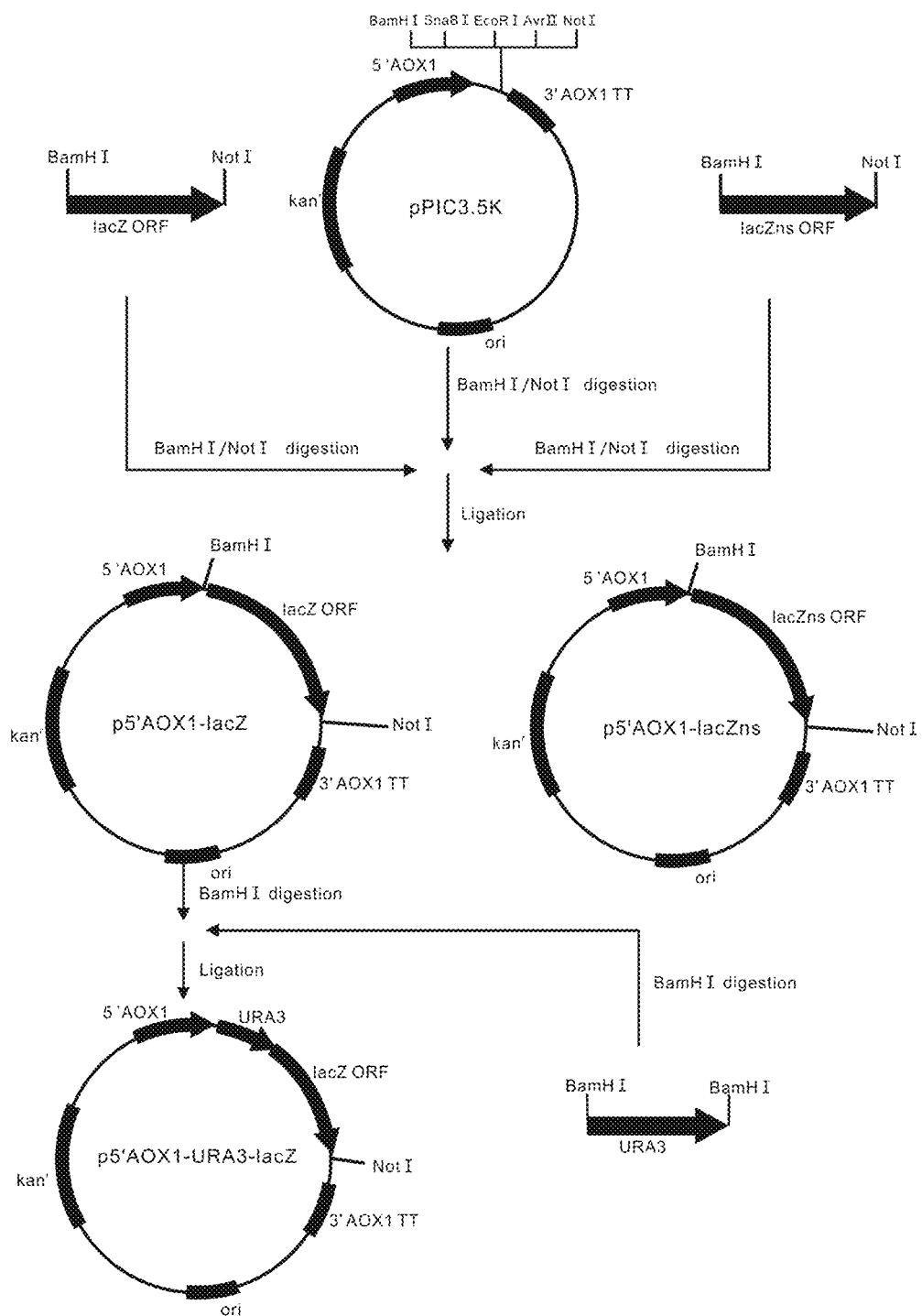

FIG. 6 depicts the scheme to construct an 5'AOX1-induced lacZ expression vector p5'AOX1-URA3-lacZ, in which URA3 is positioned between 5' AOX1 and lacZ ORF. Vector components are not drawn to scale.

Figure 7:
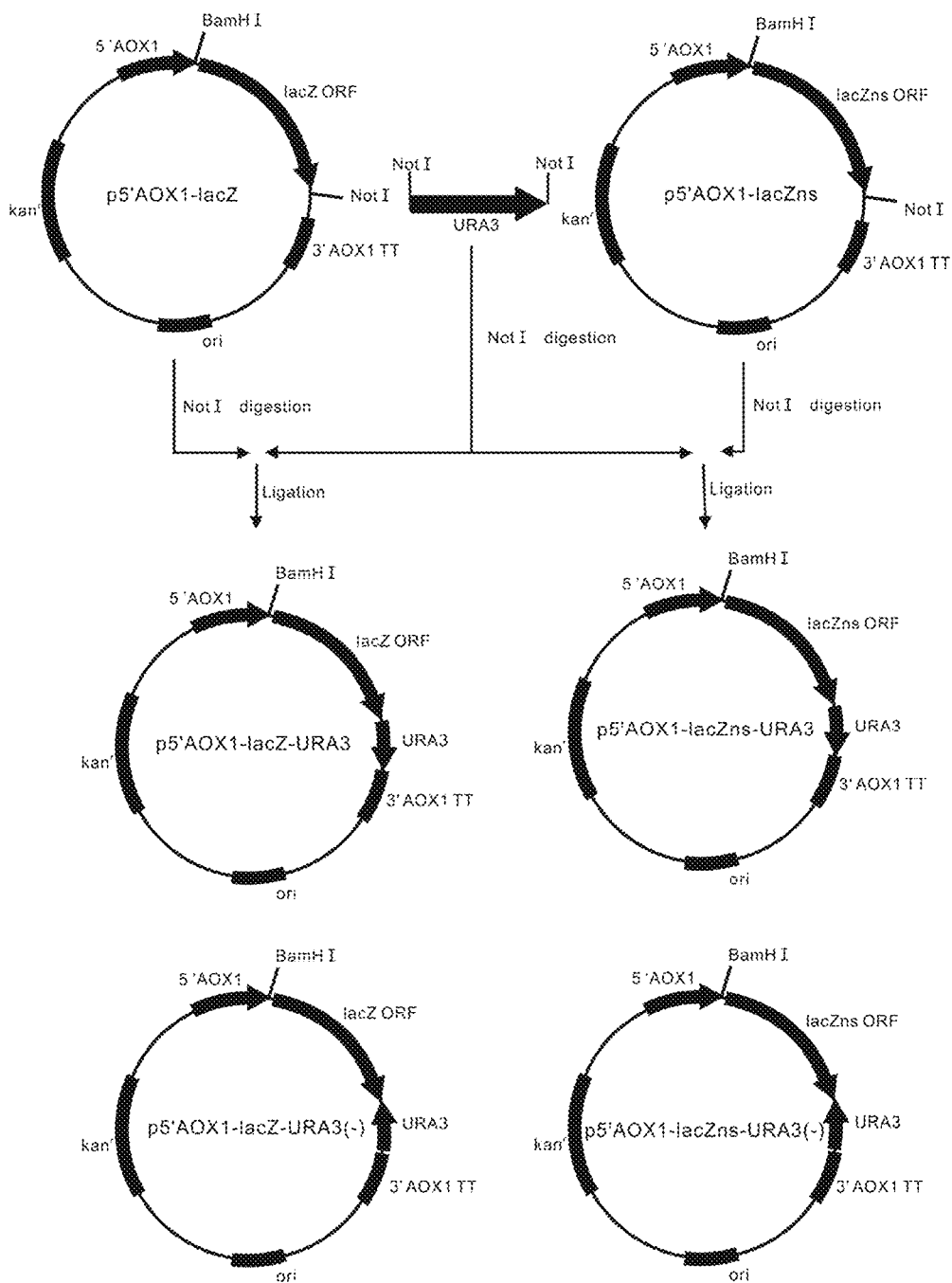

FIG. 7 depicts the scheme to construct a series of 5' AOX1-induced lacZ and lacZns expression vectors of p5'AOX1-lacZ-URA3, p5'AOX1-lacZ-URA3(−), p5'AOX1-lacZns-URA3, and p5'AOX1-lacZns-URA3(−) in which URA3 is positioned downstream of lacZ and lacZns in two orientations. Vector components are not drawn to scale.

Figure 8:
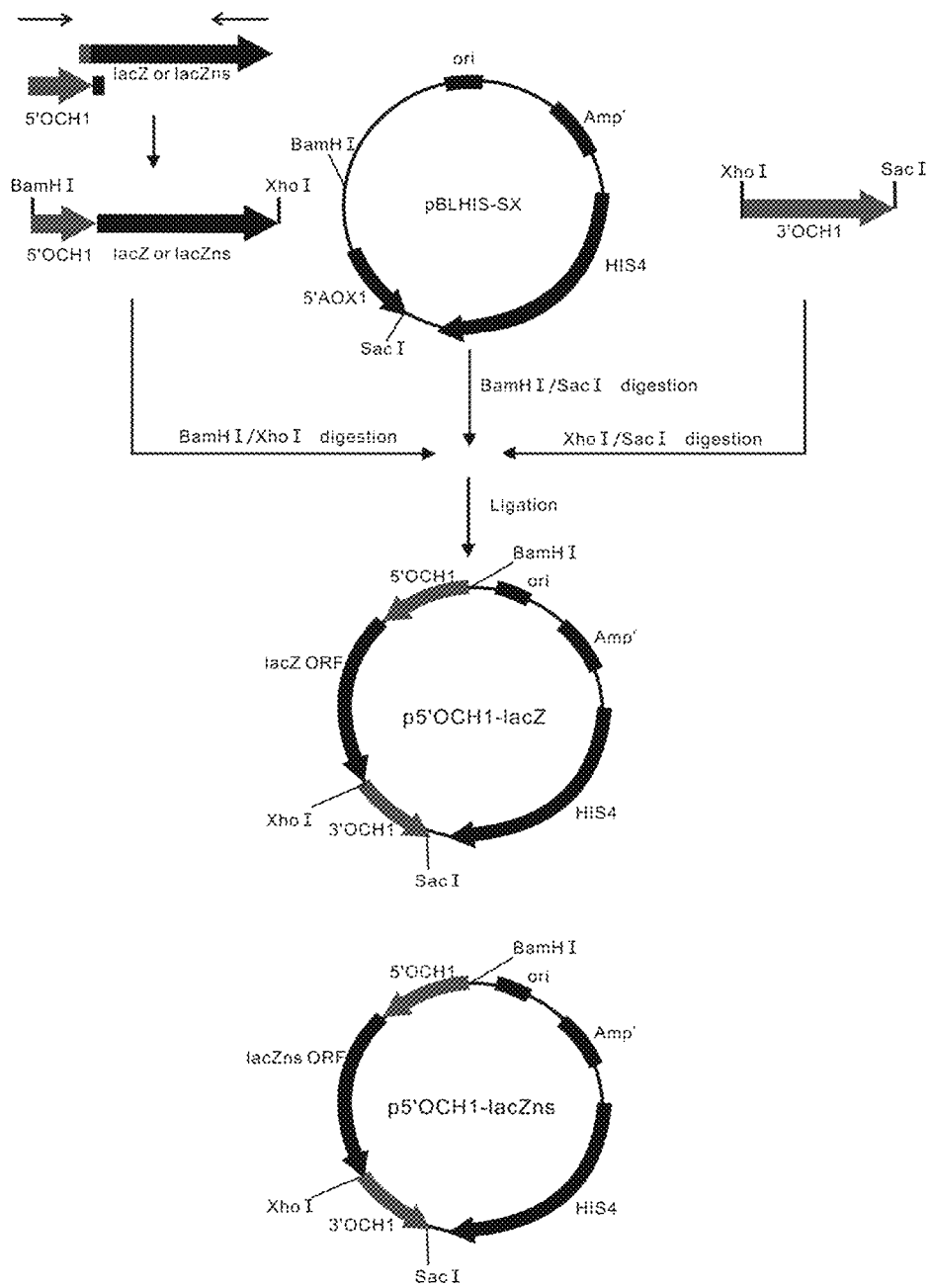

FIG. 8 depicts the scheme to construct a series of 5'OCH1-initiated lacZ and lacZns expression vectors of p5'OCH1-lacZ and p5'OCH1-lacZns. Vector components are not drawn to scale.

Figure 9:
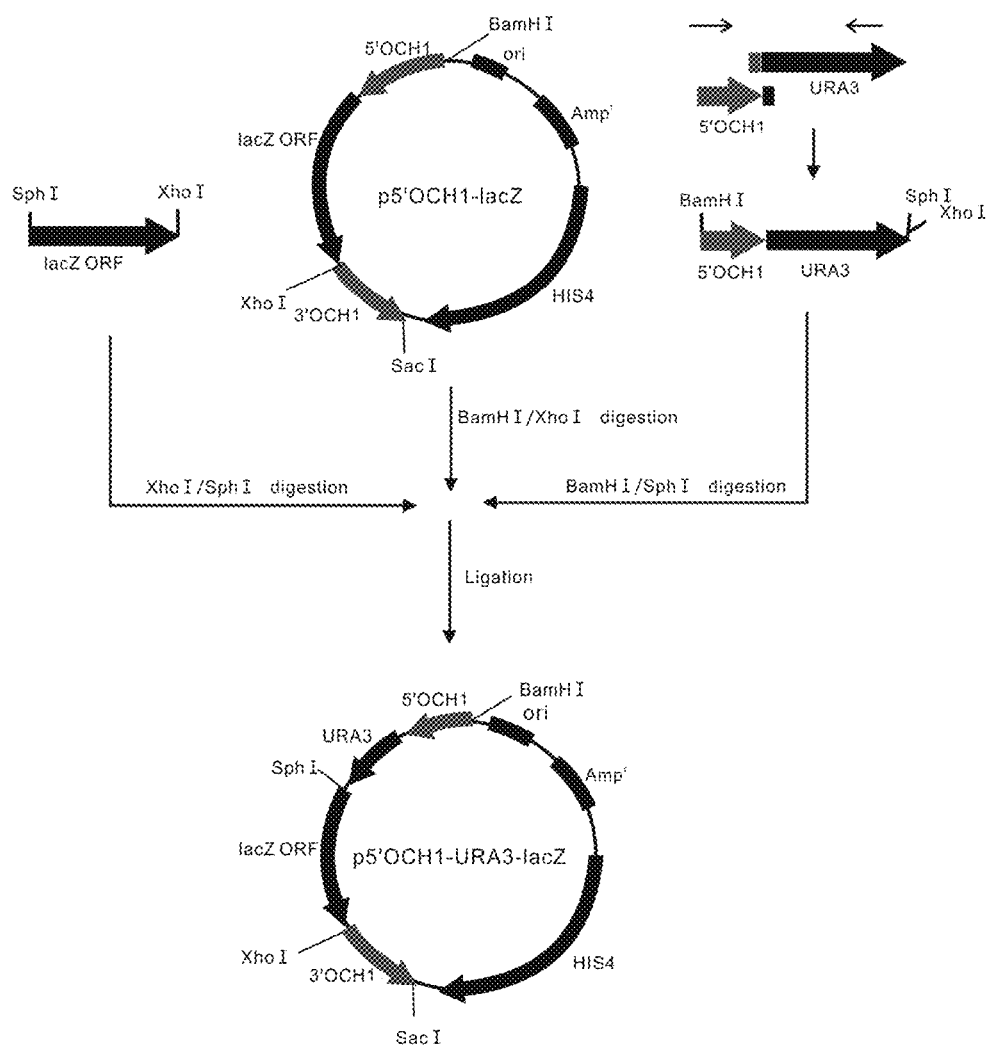

FIG. 9 depicts the scheme to construct a 5 'OCH1-initiated lacZ expression vector of p5'OCH1-URA3-lacZ, in which URA3 is positioned between 5' OCH1 and lacZ ORF. Vector components are not drawn to scale.

Figure 10:
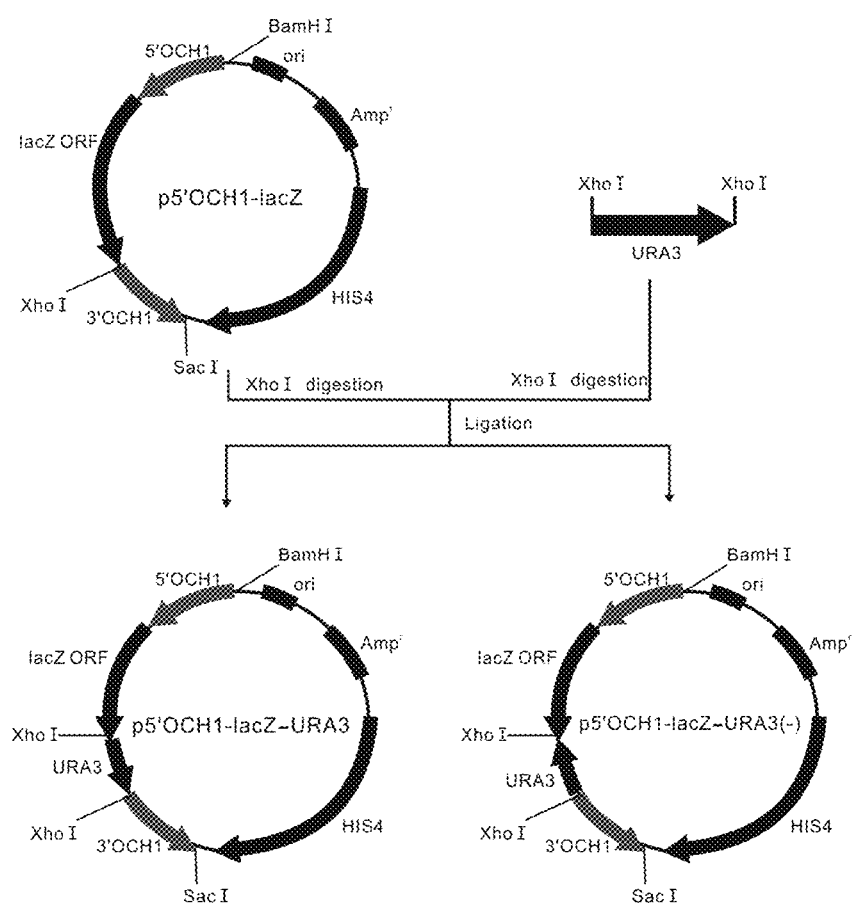

FIG. 10 depicts the scheme to construct a series of 5'OCH1-initiated lacZ expression vectors of p5'OCH1-lacZ-URA3 and p5'OCH1-lacZ-URA3(−), in which URA3 is positioned downstream of lacZ in two orientations. Vector components are not drawn to scale.

Figure 11:
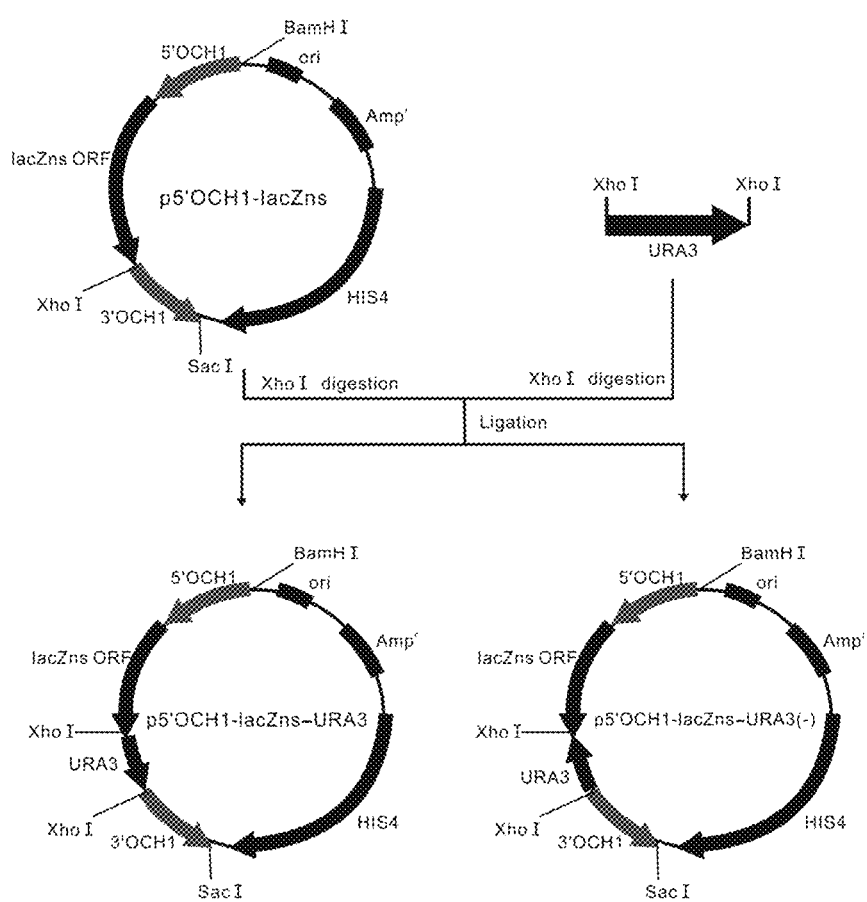

FIG. 11 depicts the scheme to construct a series of 5'OCH1-initiated lacZns expression vectors of p5'OCH1-lacZns-URA3 and p5'OCH1-lacZns-URA3(−), in which URA3 is positioned downstream of lacZns in two orientations. Vector components are not drawn to scale.

Figure 12A:
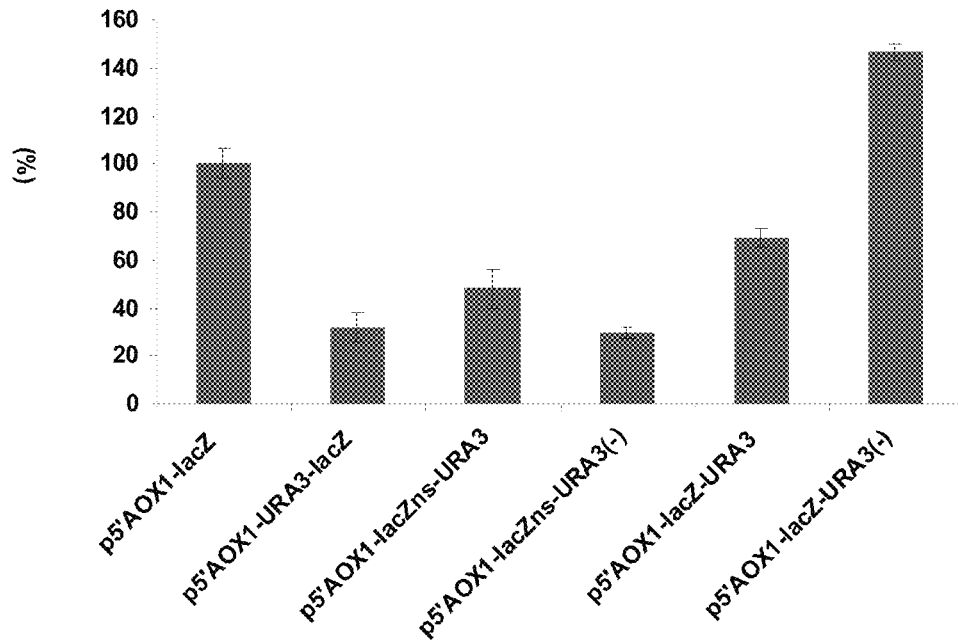
Figure 12B:
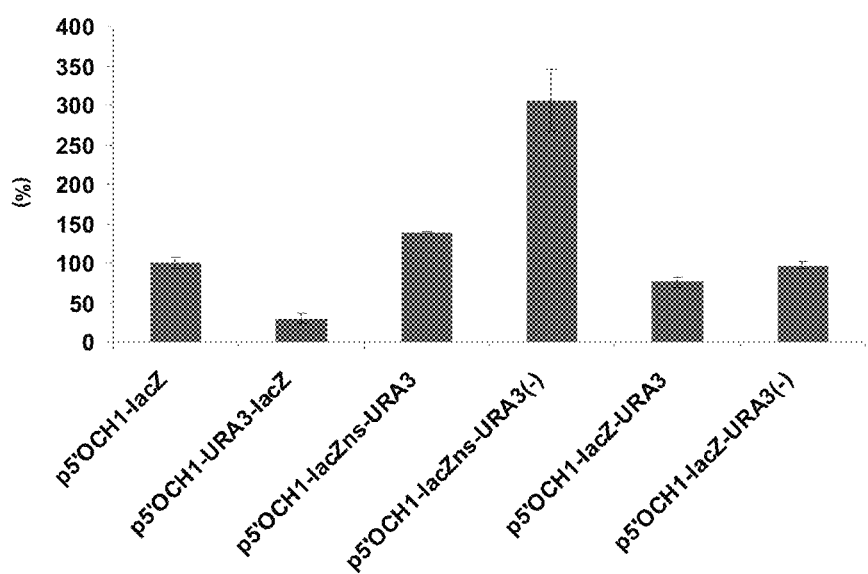

FIG. 12 shows relative lacZ mRNA expression (%). A. relative lacZ mRNA initiated by 5'AOX1 in the presence of URA3 next to start and stop codons. 100% corresponds to 5'AOX1 initiated lacZ mRNA expression without URA3 integration (p5'AOX1-lacZ). B. relative lacZ mRNA expression (%) initiated by 5'OCH1 in the presence of URA3 next to start and stop codons. 100% corresponds to 5'OCH1 initiated lacZ mRNA expression without URA3 integration (p5'OCH1-lacZ). Data are shown as the mean values±standard deviations (s. d.) from three experiments.

Figure 13A:
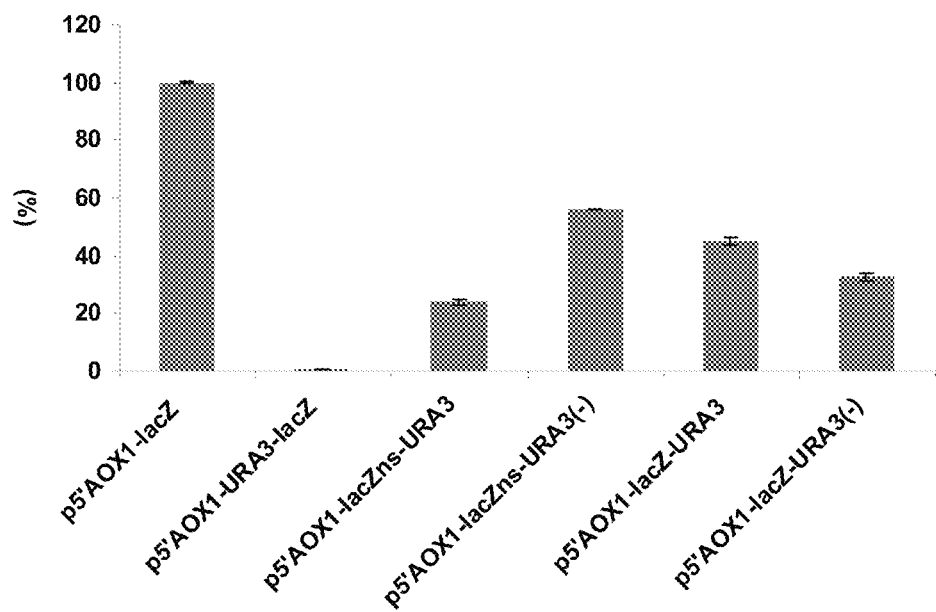
Figure 13B:
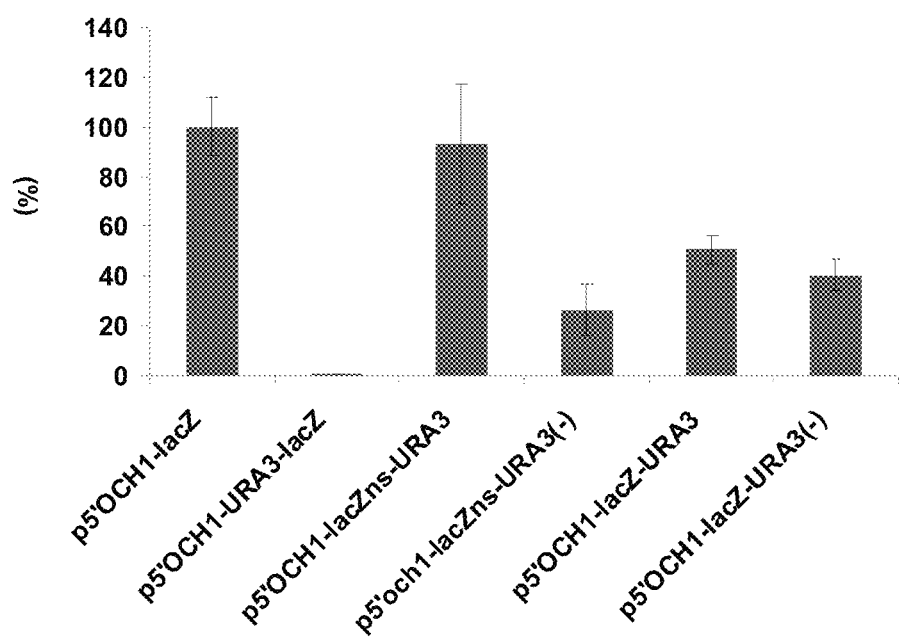

FIG. 13 shows relative intracellular specific activities of β-galactosidase (%). A. β-galactosidase activities initiated by 5'AOX1 in the presence of URA3 next to start and stop codons. 100% corresponds to 5'AOX1 initiated specific activity of β-galactosidase without URA3 integration (p5'AOX1-lacZ). B. β-galactosidase activities initiated by 5'OCH1 in the presence of URA3 next to start and stop codons. 100% corresponds to 5'OCH1 mediated specific activity of β-galactosidase without URA3 integration (p5'OCH1-lacZ). Data are shown as the mean values±standard deviations (s. d.) from three experiments.

Figure 14:
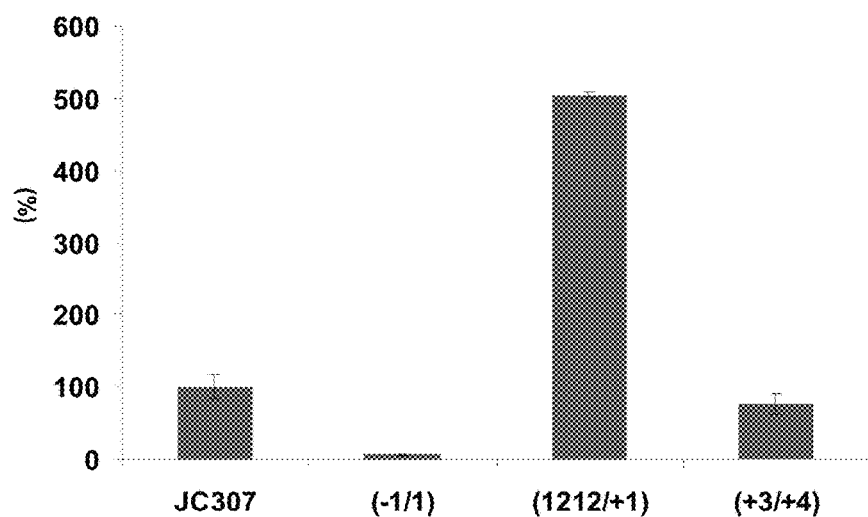

FIG. 14 shows relative OCH1 mRNA expression (%) in the strains containing gene integration next to start and stop codons. 100% corresponds to the mRNA expression in the parent JC307 strain without gene integration. Data are shown as the mean values±standard deviations (s. d.) from three experiments.

FIG. 15 shows positive-ion MALDI-TOF mass spectrum of N-glycans released from mIL-22. A. shows mass spectrum of N-glycans released from mIL-22, which is produced in GS115 strain. B. shows mass spectrum of N-glycans released from mIL-22, which is produced in strain och1(−1/+1, ADE1URA3), which has gene integration upstream of OCH1 encoding region.

MODE FOR CARRYING OUT THE INVENTION

Upon extensive and deep study, the inventors have unexpectedly found locus-independent regions for efficient HR gene targeting, and developed a gene targeting system for gene expression regulation and gene disruption. Any gene of an organism can be regulated or modified by the method of the present invention. Based on the above results, the present invention was completed.

In the present invention, the gene targeting at varies locations of a locus was systematically analyzed and regions for efficient HR gene targeting were identified. In the present invention, a gene targeting system for gene expression regulation and gene disruption was also developed. This invention exploits gene targeting by homologous recombination processes that are endogenous in the cells of all organisms, thus any gene of an organism can be regulated or modified by the method. The method can be widely used both by industrial and academic research laboratories for the regulation of gene expression, improvement of cell function, and production of heterologous proteins.

The following terms are used herein according to the following definitions.

"Gene" is used broadly to refer to any segment of nucleic acid associated with a biological function. "Peptide," "polypeptide," and "protein" are used interchangeably herein, and refer to a polymeric form of amino acids of any length. "Gene targeting" is a process for chromosomal integration of the exogenous DNA at a genetic locus, which typically results in the gene at the target locus to be modified, replaced or duplicated. It is a mechanism common to all life. "Cell" or "organism" is a term used for the organism in which gene targeting of the invention is carried out. "Cell transformation" means the exogenous DNA is introduced into cells. It is usually the result of integration of the exogenous DNA in chromosome DNA or introduction of self-replicated plasmid. "Target gene" or "target site" refers to the gene or DNA segment subject to alteration by the gene targeting method of the present invention. The target gene can be either an endogenous gene, or an exogenous DNA segment previously introduced into the organism. The target gene can be any part of endogenous genomic DNA, gene, including but not limited to a polypeptide coding region, open reading frame, regulatory region, intron, exon, or portion thereof, of the organism.

"Marker" represents a gene or sequence whose presence or absence provides a detectable phenotype of the organism.

Various types of markers include, but not limited to, selection markers, screening markers and molecular markers. Selection markers are usually genes whose expression can make the organism to have phenotype of resistant or susceptible to a specific set of conditions. Screening markers transmits a phenotype that is an observable and distinguishable trait. Molecular markers are gene sequence features that can be identified by DNA analysis.

Genes include "coding sequences", "coding regions", or "open reading frames (ORF)" that encode particular proteins or functional RNAs. A protein coding sequence is a nucleic acid sequence that is transcribed into mRNA, which in turn is translated into a protein. The boundaries of the protein coding sequence are determined by a start codon at the 5' terminus (N-terminus) and a translation stop nonsense codon at the 3' terminus (C-terminus).

Genes also include "regulatory regions" or "regulatory elements" preceding and following the coding sequence. The regulatory elements include but not limited to promoter, enhancer, intron, polyadenylation signal, 5' untranslated region (5'UTR), 3' untranslated region (3'UTR), and any derivatives thereof. Some of regulatory regions are transcribed as part of the RNA molecule, such as 5'UTR and 3'UTR. The term "5' untranslated region (5'UTR)" is intended to mean the nucleotide sequence in a mature mRNA located immediately upstream of any coding sequence and not translated into protein. The term "3' untranslated region (3'UTR)" is intended to mean the nucleotide sequence in a mature mRNA located immediately downstream of any coding sequence and not translated into protein. It extends from the first nucleotide after the stop codon of any coding sequence to just before the poly(A) tail of the mRNA. These regulatory elements can control a wide variety of processes including but not limited to transcription (e.g., initiation, elongation, and/or termination), translation (initiation, elongation, and/or termination), and RNA stability, etc.

"Promoter" is a nucleic acid regulatory region capable of binding RNA polymerase and initiating transcription of a downstream (3' direction) coding sequence. The promoter sequence is bounded at its 3' terminus by the transcription initiation site and extends upstream (5' direction) to include the minimum number of bases or elements necessary to initiate transcription. Within the promoter sequence will be found a transcription initiation site, as well as protein binding domains responsible for the binding of RNA polymerase. Eukaryotic promoters will often, but not always, contain "TATA" boxes and "CAT" boxes, while prokaryotic promoters often contain the consensus sequence TATAAT. Many promoters are called constitutive promoters as they are active in all circumstances in the cell, but some are inducible promoter whose activity is regulated in response to specific stimuli.

"Terminator" is a segment of a nucleic acid sequence which provides signals during transcription to trigger transcription machine for releasing newly synthesized mRNA (or RNA) and terminating transcription. In prokaryotic transcription, two classes of transcription terminators, Rho-dependent and Rho-independent sequences, are responsible for triggering the end of transcription. In eukaryotic transcription of mRNAs, transcription machine recognizes the terminator signals and triggers the termination process for releasing mRNA, and then poly(A) sequence is added to the 3' end of the mRNA through polyadenylation.

Regulation on transcription can be divided into two categories according to its action nature: the first category is inhibition of DNA template function, that is, changing the template function by inhibiting molecules from binding to DNA; the second category is inhibition of RNA polymerase, that is, inhibiting the binding of molecules to RNA polymerase to inhibit its activity (Sandhya Payankaulam, Li M. Li, and David N. Arnosti (2010) Transcriptional repression: conserved and evolved features. Curr Biol. 14; 20(17): R764-R771). However, these control methods can not be used as a general method to specifically regulate expression of any target genes.

"Translation" is the process in which mRNA molecule is used as a template to synthesize a protein. A mature mRNA composed of three parts, including 5' UTR, ORF, and 3' UTR. The 5' UTR is scanned by the translation initiation complex in a 5' to 3' direction until an initiator AUG codon is encountered. At this position, ribosome is ready to decode mRNA and initiates to add amino acids to produce a specific protein. As a stop codon (UAA, UAG or UGA) is encountered by ribosome, the protein synthesis is terminated and the protein is released from the ribosome.

Translation process can be controlled by RNA-binding proteins (RBPs) and small RNAs, that bind to the mRNA and modify its translatability. RBPs bind to specific elements that are usually located in the 5' or 3' UTRs to activate or repress translation. However elements within 5' UTRs are in the path of the scanning/translating ribosome, which can displace regulatory factors before they exert their effects to regulate translation. In global measurements of decay and translation rates for mRNAs, the 3' UTR elements with the greatest implied influence are microRNA complementary sites, which are associated with repression of 32% and 4% at the stability and translational levels, respectively. However 3' UTR has limited influence on the stability and translational efficiency of most mRNAs (Noah Spies, Christopher B. Burge, and David P. Bartel (2013), 3' UTR-isoform choice has limited influence on the stability and translational efficiency of most mRNAs in mouse fibroblasts, Genome Research, 23:2078-2090). Therefore, it seems to be an inefficient method to regulate protein translation by altering 5' and 3' UTR.

Cells have surveillance systems that recognize and eliminate aberrant mRNAs to avoid the production of potentially harmful protein products. For example, cells can recognize an aberrant mRNA lacking a stop codon (nonstop mRNA) and form the Ski complex at the 3' end to mediate the degradation of the nonstop mRNA. This nonstop mRNA decay may avoid production of potentially deleterious extended products that could have dominant-negative activity against wild-type gene products (van Hoof A, Frischmeyer P A, Dietz H C, Parker R (2002) Exosome mediated recognition and degradation of mRNAs lacking a termination codon. Science 295: 2262-2264).

In practice, there is currently no effective way to regulate the expression of genomic genes. Any methods and/or tools to predictably control the expression of any target gene would be beneficial for biological research and numerous biotechnology applications. Gene targeting technology is a process for chromosomal integration of the exogenous DNA at a genetic locus, which causes the gene at the target locus to be modified, replaced or duplicated.

"Ends-in" and "ends-out" refer to the two different arrangements of exogenous DNA that can be use for integration into the genome via homologous recombination. In gene targeting by "ends-in" recombination, the ends of linear exogenous DNA point toward each other when paired with a region of homology in genome locus, and integrate the DNA in the genome by single cross-over recombination (roll in), thereby producing repeating sequences in the same direction of the target gene. However, exogenous DNA may be excised via homologous recombination between repeated target genes, and the initial wild-type state of the target gene can be restored. In gene targeting by "ends-out" recombination, the ends of linear exogenous DNA point away from each other when paired with the homologous target in genome locus, and insert the DNA into the genome by double cross-over recombination between the terminal targeting flanks and the homologous chromosomal host genome sequence. Ends-out targeting is frequently used in mice and yeast because it gives a straightforward route to replace or delete a target locus. However, ends-out events are less efficient than ends-in events (Paques and Haber 1999, Microbiology and Molecular Biology Reviews, 63: 349-404). In the present invention, gene targeting refers to the "ends-out" double cross-over homologous recombination, unless it is specifically indicated as ends-in targeting by single cross-over (roll-in).

Gene targeting is a process common to all life and can be used for any gene, regardless of its transcriptional and translational activity. However, the technology is constrained by two limitations: the low rate of homologous recombination and the high rate of random (non-targeted) integration.

Gene targeting occurs via two distinctively different molecular mechanisms: homologous recombination (HR) pathway and non-homologous end-joining (NHEJ) pathway. Both recombination pathways are mediated via the repair of DNA double-strand breaks (DSBs). In HR gene targeting, an exogenous DNA fragment, usually a selectable marker gene with homologous sequences at each end, is precisely integrated at its homologous chromosomal counter-part. But in NHEJ pathway, an exogenous DNA fragment with selectable marker gene will randomly integrate at nonhomologous chromosomal sites. The efficiency of site-specific gene targeting is generally determined by the relative strength between HR and NHEJ pathways.

The efficiency of homologous recombination genes targeting in different biological systems is also significantly different. Conventional yeast, *Saccharomyces cerevisiae* and fission yeast, *Schizosaccharomyces pombe*, have very efficient HR gene targeting systems. In *Saccharomyces cerevisiae*, the frequency of gene replacement events can be as many as 95% of the total transformants when the targeting fragments are 30 to 45 bp (Paques and Haber 1999, Microbiology and Molecular Biology Reviews, 63: 349-404). However, most of organisms have very low efficiencies in HR gene targeting. The gene targeting efficiencies in methylotrophic yeast. *Pichia pastoris* and other "non-conventional" yeasts, including *Hansenula polymorpha, Yarrowia lipolytica, Pichia stipitis* and *Kluyveromyces lactis*, can be extremely low. The frequency of gene replacement event is highly dependent on the length of the targeting fragment. The frequency can be less than 0.1% when the targeting homologous sequences are less than 500 bp, but it can be greater than 50% for some target sites when extensive 1 kb targeting fragments are used (Klinner U, et al (2004) *Ferns Microbiology Reviews* 28: 201-223; Gregg J M (2010) *Pichia* Protocols, Second edition. Totowa, N.J.: Humanna Press). The efficiency in HR gene targeting in most of organisms, including fungi and eukaryotic organisms is very low.

In addition, the efficiency of HR gene targeting in strains with the same genetic background can be locus dependent. For example, the disruptions of ARG1, ARG2, ARG3, HIS1, HIS2, HIS5 and HIS6 in *P. pastoris* GS115 strain occur at a high frequencies of 44-90% when the lengths of homologous sequences are range within 200 to 900 bp (Nett, et al (2005) Yeast 22: 295-304). But the deletion of OCH1 and SGS1 in *P. pastoris* is significantly low efficient at a frequency of <1% when~1 kb or more regions of homology are used (Chen Z, Sun H, Li P, He N, Zhu T, et al. (2013) Enhancement of the Gene Targeting Efficiency of Non-Conventional Yeasts by Increasing Genetic Redundancy. PLoS ONE 8(3): e57952). The molecular mechanism for this locus dependent phenomenon is not well understood. One possible reason is that there are hotspot regions along each chromosome and homologous recombination is positioned preferentially at hotspots (Wahls et al. Plos One 3:e2887).

While it is well known that the efficiency of HR gene targeting can be dependent on competition between HR and NHEJ, genomic locus and organism system, little is know about the HR targeting at different positions in coding and regulatory regions of locus, especially for genes which are difficult to be disrupted.

In the present invention, OCH1, an inefficient targeting locus, and ADE1, a common targeting locus, were used as models to systematically analyze HR targeting at varies locations in genome locus. This study can facilitate the development of gene targeting technology system for gene expression regulation and gene disruption.

In the present invention, targeting vectors, comprising the parts of selection markers, homologous regions, and replication origin were developed. These parts can be joined to form a circular vector. The circular vector may contain other parts and linkers between the parts if necessary. However, the invention is intended to include other forms of targeting vectors as well, which function equivalent. Targeting vector may also be named as vector. In general, vectors used in recombinant DNA technology are often in a form of "plasmid". In the present specification, the term "vector" and "plasmid" are used interchangeably.

The presence or absence of marker, which refers to a gene or sequence, provides a detectable phenotype of the organism. One or more markers may be used in order to select and screen for gene targeting events. Various types of markers useful for this invention include, but not limited to, selection markers, screening markers and molecular markers.

Expression of selection marker genes can make an organism to have phenotype of resistant or susceptible to a specific set of conditions. Selection markers include genes carrying resistance to an antibiotic such as kanamycin, hygromycin, zeocin, bleomycin, spectinomycin, streptomycin, gentamycin, et al.

Selectable marker systems composed of an auxotrophic mutant host strain and a wild-type biosynthetic gene which complements the host's defect on an incomplete media such as HIS4, LEU2, URA3, ADE1, LYS2 and TRP1 genes in yeast, and other genes known in the art. For transformation of *P. pastoris* his4 strains, for example, the *S. cerevisiae* or *P. pastoris* HIS4 gene may be employed.

Screening markers transmits a phenotype that is an observable and distinguishable trait. Screenable markers include fluorescent proteins such as green fluorescent protein (GFP), reporter enzymes such as β-galactosidase (lacZ), alkaline phosphatase (AP), β-lactamase, β-glucuronidase, glutathione 5-transferase (GST), lucifera, and others known in the art.

Molecular markers are gene sequence features that can be identified by DNA analysis.

The marker genes are flanked by two homologous recombination regions. The upstream-side one of the homologous recombination regions is homologous to a region upstream of the target gene, and the downstream-side one of the homologous recombination regions is homologous to a region downstream of the target gene. One or more marker genes between upstream homologous recombination region and downstream homologous recombination region can be connected in the same or opposite direction.

The homologous recombination region allows the recombination site to be located between the first nucleotide of the start codon of the gene to be regulated and the $110^{th}$, preferred $50^{th}$ nucleotide upstream from the first nucleotide of the start codon of the gene to be regulated, or the 5' and 3' homologous sequences allow the recombination site of the nucleotide construct to be located between the $100^{th}$, $50^{th}$ or $20^{th}$ preferred $50^{th}$ nucleotide upstream from the first nucleotide of the stop codon of the gene to be regulated and the $300^{th}$ nucleotide downstream from the first nucleotide of the stop codon of the gene to be regulated.

Herein, a region that is "homologous" to the corresponding gene region means a region that has a sequence at least 90%, preferably at least 92%, more preferably at least 94%, still more preferably at least 96%, still more preferably at least 98%, still more preferably at least 99%, and most preferably at 100% identical to the base sequence of the region referred to. Preferably, this "homologous region" is derived from the region referred to.

The length of the homologous recombination regions is not particularly limited. It is preferable that a region has a length suitable for allowing homologous recombination to occur. Therefore, the region may have a length of at least 40 base pairs.

When it is contemplated to pass a vector of the invention though bacterial cells, it is desirable to include a bacterial origin of replication and antibiotic resistant genes to in the vector, to ensure the maintenance of the vector from generation to generation of the bacteria. Bacterial origins (ori) of replication include the fl-ori, colisin, col El, and others known in the art. Genes carry resistant to antibiotic such as ampicillin, kanamycin, Zeocin, and others known in the art. The origin of replication and antibiotic resistant gene can be linked between different parts.

In the present invention, a linear targeting cassette is provided, which can be linearized from targeting vector by restriction enzyme digestion or can be chemically synthesized in the gene of art. This "targeting cassette" may also be called herein a "targeting fragment", or "fragment for gene disruption or gene integration" for convenience. This targeting cassette is used to disrupt a target gene and integrate exogenous genes into chromosome of host such that exogenous genes can perform functions in the host.

The essential parts of targeting cassette include marker gene, and homologous regions. The targeting cassette may contain other parts and linkers between the parts if necessary. The marker gene is flanked on upstream and downstream sides by homologous regions.

The targeting cassette or vector is introduced into host cells for homologous recombination. Transformation and transfection of host cells may be carried out according to a method well known to those skilled in the art.

Suitable methods of transformation include viral infection, transfection, conjugation, protoplast fusion, electroporation, particle gun technology, calcium phosphate precipitation, direct micro injection, and the like. The choice of method is generally dependent on the type of cell being transformed and the circumstances under which the transformation is taking place. A general discussion of these methods can be found in Ausubel, et al., Short Protocols in Molecular Biology, 3rd ed., Wiley & Sons, 1995.

For example, yeast transformation can be performed with different procedures including, spheroplast procedure, electroporation, polyethylene glycol procedure, alkali cation procedure and the like [Gregg J M (2010) *Pichia* Protocols, Second edition. Totowa, N.J.: Humanna Press].

Examples of the host cell useful in the present invention include typical eukaryotic and prokaryotic hosts, such as *E. coli, Pseudomonas* spp., *Bacillus* spp., *Streptomyces* spp., fungi, yeasts, such as *S. cerevisiae, P. pastoris*, insect cells, such as *Spodoptera frugiperda* (SF9), animal cells, such as CHO and mouse cells, African green monkey cells, cultured human cells, and plant cells. Yeasts are preferably host cells in the present invention. *P. pastoris* is more preferable host cells.

The transformed cells were then selected based on phenotype of selectable marker.

In the present invention, site-specific homologous recombination integrations at 5'-regulatory region, coding region, and 3'-regulatory region were evaluated, and regions for high frequency of gene integration were identified. In contrast to previous reports that the efficiency of HR gene targeting is genome locus dependent when 1 kb or more regions of homology are used, the present invention finds that the efficiency of HR gene integration at 5'- and 3'-regulatory regions is locus independent and at significant high level when less than 1 kb homology is used. In addition, the frequency of gene integration in 3' end of coding region is higher than in other coding region. The frequency of targeting integration in different regions of genome locus can be expressed in following order: 5'-regulatory region and 3'-regulatory region>>3' end of coding region>other coding region.

In the present invention, methods to precisely control target gene expression by gene integration at 5'-regulatory region were developed. Integration gene can be any marker gene, including selectable marker systems, screening markers, and molecular markers, which will help to identify transformants with gene integration. The ORF of marker gene can be fused with different promoters, secreted signal sequences (if required) and transcription terminators in a certain position and orientation to form an expression cassette. The arrangement and orientation of these segments are known to a skilled person in the art. These marker gene expression cassettes can be integrated at any positions in 5'-regulatory region in both strands of DNA and in same or opposite orientation to target ORF, more preferable at positions in 5'-regulatory region proximal to target ORF, and most preferable at the position immediately upstream of the target ORF in the same strand and same orientation. The ORF of marker gene and transcription terminator can be fused and integrated into 5'-regulatory region proximal to target ORF, most preferred to integrate at positions immediately upstream target ORF in the same strand and same orientation, so that 5'-regulatory region of target gene can be utilized to initiate expression of marker genes.

Gene integration at 5' regulatory region, especially at position immediately upstream of ORF, can efficiently suppress the efficiency of transcription and translation, thus expression of a specific target gene. At present, the methods of regulating gene transcription mainly include: altering template function by inhibiting the binding of molecules to DNA, and inhibit transcriptional activity by inhibiting the binding of molecules to RNA polymerase. Gene integration in genomic locus, especially upstream of ORF, is a much more efficient method to precisely control the target gene expression than currently used methods, in which small RNAs and RNA-binding proteins are used for binding to mRNA to change its translatability.

In another way, any target ORF expression can be up-regulated by integrating targeting cassettes, which consist of selection marker cassettes fused at downstream with strong promoters, at any positions in 5' region proximal to the target ORF start codon, more preferable at the upstream of start codon, and most preferable at the positions 3-10 base upstream of start codon.

In accordance with another aspect, methods to reduce the target ORF gene expression was developed in the present invention by integrating selection marker cassettes at 3'-regulatory region in both strands at the same or opposite orientation, most preferable at the position immediately downstream of the stop codon.

In accordance with another aspect, methods to reduce the target ORF gene expression was developed in the present invention by integrating selection marker cassettes proximal to the 3' end of coding region in both strands at the same or opposite orientation.

Table 1 compares homologous recombination integration efficiencies at different positions in OCH1 and ADE1 genes of *Pichia pastoris*. These positions are determined by the nucleotide number of the genomic gene, which refers to the corresponding initiation codon of the coding region as nucleotides 1-3 and the corresponding stop codons as nucleotides +1 to +3. The correct integron is a clone with the correct gene integration verified by PCR. Targeting efficiency is defined as the ratio of the correct integrons verified by PCR to the total clones examined.

TABLE 1

| Locus | Integration postion | Length of homologous sequence (bp) (5'H/3'H) | Correct integron | Examined clones | Targeting efficiency |
|---|---|---|---|---|---|
| OCH1 | −110/−109 | 600/600 | 8 | 20 | 40% |
|  | −1/1 | 600/600 | 7 | 20 | 35% |
|  | 553/554 | 600/600 | 0 | 100 | <1% |
|  | 1096/1097 | 600/600 | 0 | 100 | <1% |
|  | 1165/1166 | 600/600 | 0 | 100 | <1% |
|  | 1212/+1 | 600/600 | 4 | 60 | 7% |
|  | +3/+4 | 600/600 | 16 | 20 | 80% |
|  | +203/+204 | 600/600 | 5 | 20 | 25% |
| ADE1 | −110/−109 | 785/800 | 10 | 20 | 50% |
|  | −1/1 | 800/800 | 13 | 20 | 65% |
|  | 703/704 | 800/800 | 3 | 100 | 3% |
|  | 862/863 | 800/800 | 3 | 20 | 15% |
|  | 912/+1 | 850/750 | 16 | 20 | 80% |
|  | +3/+4 | 853/747 | 6 | 20 | 30% |
|  | +203/+204 | 800/800 | 9 | 20 | 45% |

According to the gene targeting method of the present invention, a skilled person can engineered a strain; in particular, a gene in a strain, homologous recombination efficiency of which is lower than 3%, preferably 1% by the conventional targeting method, can be engineered. As can be seen from the above table, the target efficiency of homologous recombination integration at certain intergration position by using the method of the invention is much higher than that obtained by a conventional targeting method.

Additionally, a method for engineering a strain is provided in the present invention, and the engineered strain can be used in preparation of recombinant proteins. In a specific embodiment, the glycosylation pattern in the recombinant protein is altered. For example, the glycosylation pathway of a protein in a strain can be altered by disrupting OCH1 gene; and degradation of the recombinant protein can be reduced by disrupting the gene of protease in a strain, etc. The gene targeting method of the present invention can be applied to engineering the biological metabolic reaction of a strain, thereby more efficiently producing metabolites. Moreover, the gene targeting method of the present invention can be applied to alter the enzymatic activity in an organism so that the engineered organism can carry out bio-catalytic reactions more efficiently. A strain engineered by the method of the present invention can also be used in various fields, such as metabolic engineering, genetic research and biotechnology applications.

Advantages of the Present Invention:
1. Locus-independent regions for efficient HR gene targeting in identified in the invention;
2. Any gene in an organism can be engineered by the method of the invention;
3. The method of the present invention can be widely used in the field of biotechnology industry and biology to regulate gene expression, improve cell function and produce heterologous protein.

EXAMPLE

Materials

The chemicals, enzymes, media and solutions used for the creation, verification and application of the libraries are commonly used and well known for a person skilled in the art of molecular and cell biology; they are available from a number of companies including Thermo Fisher Scientific, Invitrogen, Sigma, New England BioLabs. Takara Biotechnology, Toyobo, TransGen Biotech, and Generay Biotechnology et al. Many of them are provided in kits. pPIC3.5K and pPICZ vector are from Invitrogen. pBLHIS-SX, pBLURA-SX, pBLADE-SX vector was obtained from Keck Graduate Institute, Claremont, Calif. *E. coli* strain Trans1-T1 was obtained from TransGen Biotech. *Pichia pastoris* auxotrophic strains JC301 (ade1 his4 ura3) and JC307 (his4 ura3) are obtained from Keck Graduate Institute (KGI), GS115 (his) from Invitrogen. Nucleotide sequence data were primarily obtained from the public database NCBI (www.ncbi.nih.gov).

Method

Unless indicated otherwise, the methods used in this invention including Polymerase Chain Reaction (PCR), restriction enzyme cloning, DNA purification, bacterial and eukaryotic cell cultivation, transformation, transfection, and Western blotting were performed in a standard manner well known for a person skilled in the art of molecular and cell biology, and such as described in the following manuals: Sambrook J et al. (Molecular Cloning A Laboratory Manual (Third Edition), Cold Spring Harbor Laboratory Press, Cold Spring Harbor, N.Y., 2001), Ausubel F M et al. (Current Protocols in Molecular Biology, Wiley InterScience, 2010), and Gregg J M (*Pichia* Protocols, (Second edition), Totowa, N.J.: Humanna Press, 2010).

An *E. coli* strain Trans1-T1 was used for the construction and amplification of plasmids. The strain was grown in Luria-Bertani (LB) medium (10 g/L of tryptone, 5 g/L of yeast extract, and 5 g/L of sodium chloride) or LB plate (15 g/L agar) with appropriate antibiotic. Antibiotics were added at the following concentrations: 100 mg/L of ampicillin, 50 mg/L kanamycin, and 25 mg/L Zeocin).

*P. pastoris* strains were grown in YPD medium (10 g/L yeast extract, 20 g/L peptone, 20 g/L dextrose) and YPD plate (10 g/L yeast extract, 20 g/L peptone, 20 g/L dextrose, 15 g/L agar). *P. pastoris* auxotrophic strains were selected on YNB medium without amino acids (67 g/L yeast nitrogen base, 5 g/L dextrose) and YNB plate without amino acids (67 g/L yeast nitrogen base, 5 g/L dextrose, 15/L agar), antibiotics supplemented as appropriate. Some *P. pastoris* auxotrophic strains were selected on SC medium (8 g/L SC without histidine and uracil, 20 g/L dextrose) and SC plate (8 g/L SC without histidine and uracil, 20 g/L dextrose, 15l agar), antibiotics supplemented as appropriate. Antibiotics were added at the following concentrations: 500 mg/L G-418 sulphate, and 100 mg/L Zeocin).

Genomic DNA was extracted from *P. pastoris* by using lithium acetate-SDS lysis followed by ethanol precipitation, which is described in the following publication: Looke et al. 2011, Biotechniques. 50: 325-328.

Transformation of *Pichia pastoris* was performed by electroporation with MicroPulser™ electroporation apparatus following manufacturer (BioRad) operating instructions.

Example 1

Construction of a Basic Vector

Figure 1:
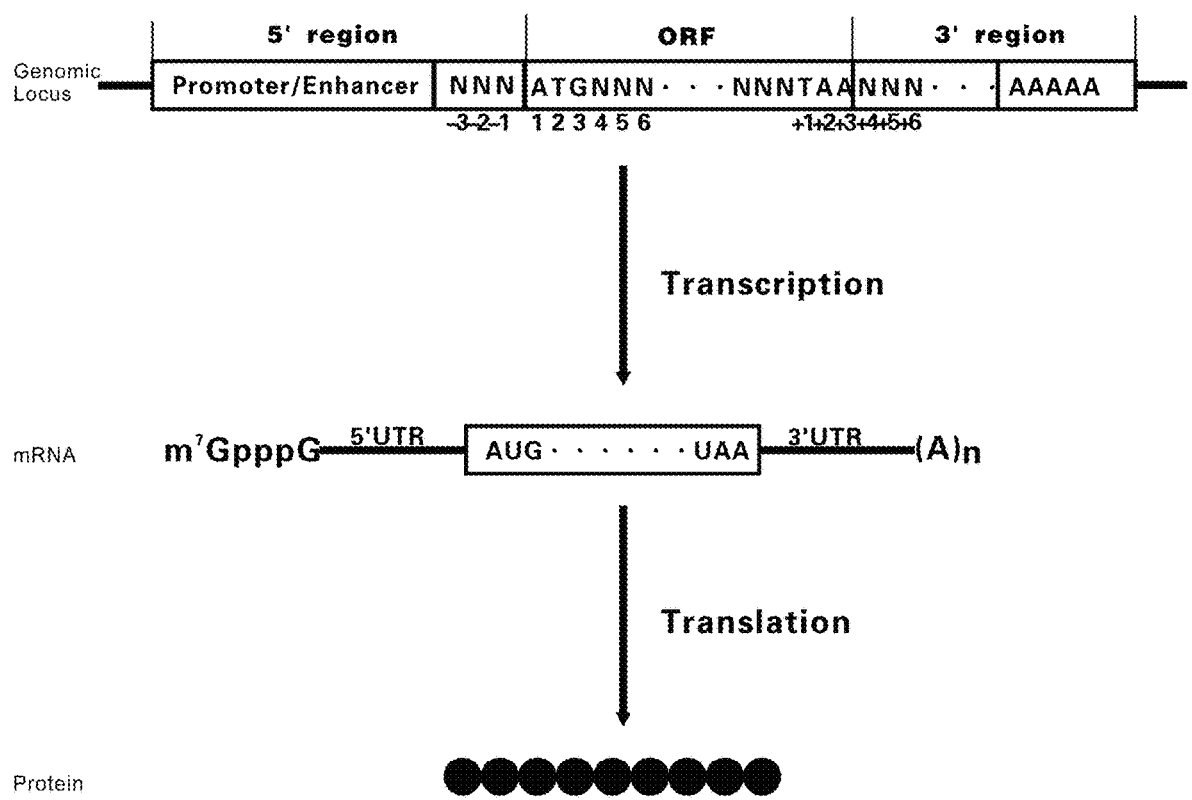
FIG. 1 Diagram of a typical gene includes 5' regulatory region (5' region), open reading frame (ORF), and 3' regulatory region (3' region). Promoters and enhancers determine what portions of the gene will be transcribed into the messenger RNA (mRNA). 5' and 3' UTRs regulate the translation process from mRAN to protein. The numbering of the nucleotide for the 5'- and 3'-regions refers to the respective start codon of the coding region as nucleotides 1-3 (5' upstream area numbered with "−") and the respective stop codon as nucleotides +1 to +3 (3' downstream area numbered with "+"). Gene components in the vector are not drawn to scale.
Figure 2:
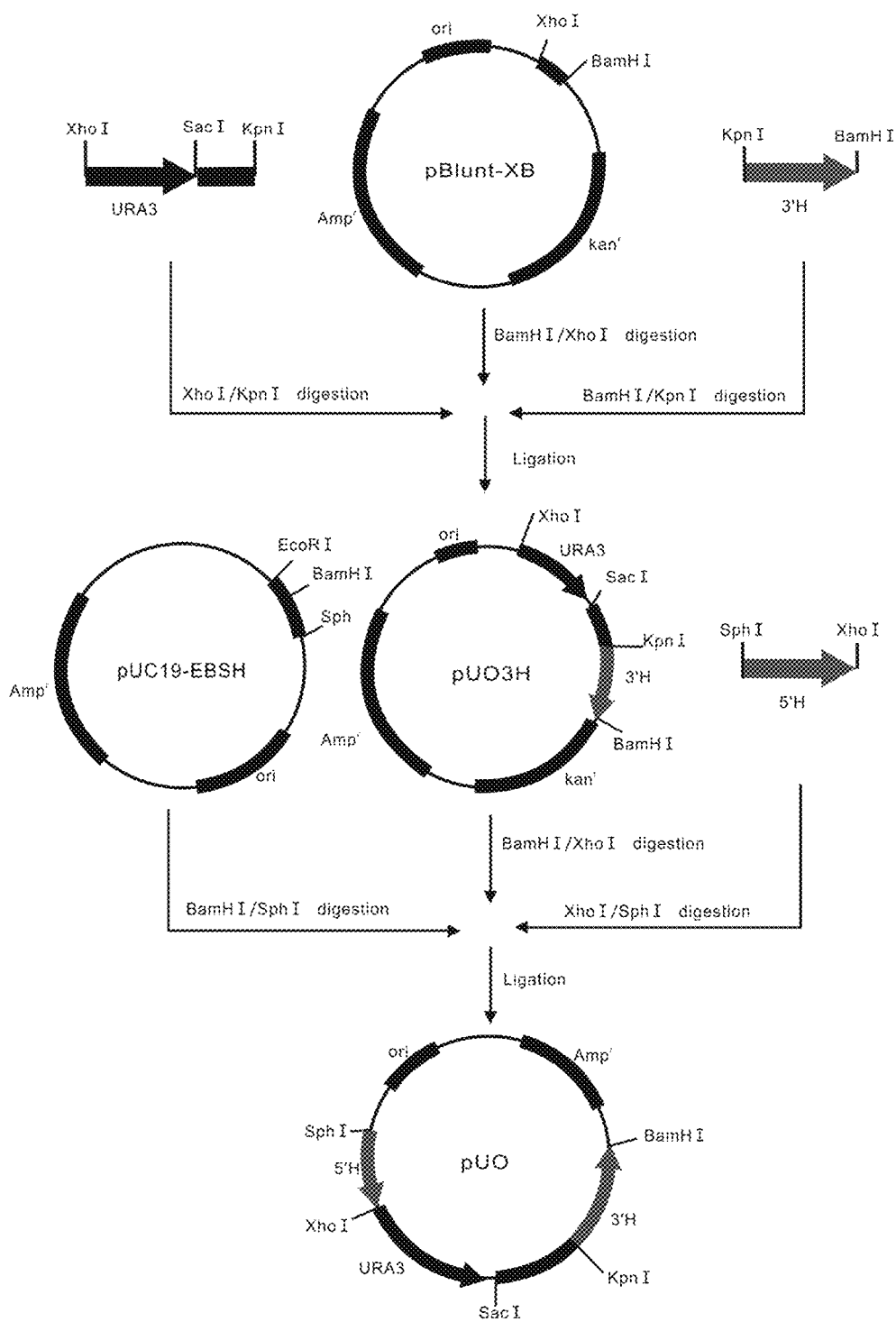
FIG. 2 depicts a scheme to construct a vector of pUO. Vector components are not drawn to scale.

FIG. 2 depicts a scheme to construct a vector of pUO.

PCR1, KpnIOch1(+54) F (SEQ ID NO: 1, the primer has a Kpn I restriction enzyme site) and Och1(+801)BamHI R (SEQ ID NO: 2, the primer has a BamH I restriction enzyme site) primer pair were used for PCR amplification of *Pichia pastoris* OCH1 3' sequence (3'H) using genomic OCH1 gene as a template;

PCR2, XhoIURA3 F (SEQ ID NO: 3, the primer has a Xho I restriction enzyme site) and DRKpnI R (SEQ ID NO: 4, the primer has a Kpn I restriction enzyme site) primer pair were used for PCR amplification of *Pichia pastoris* URA3 expression cassette and SacI-KpnI fragment using pBlunt-URA3SK vector as a template. The pBlunt-URA3SK vector was obtained by ligating a PCR fusion fragment of URA3 and SacI-KpnI fragment to pBlunt vector (TransGen Biotech, China).

Next, the PCR products of OCH1 3'H was digested with Kpn I and BamH I, and URA3 expression cassette was digested with Xho I and Kpn I, respectively. The KpnI-BamHI fragment of OCH1 3'H and the XhoI-KpnI fragment of URA3 expression cassette were inserted into the Xho I and BamHI sites of pBlunt-XB vector to create pUO3H vector. The pBlunt-XB vector was obtained by ligating a fragment with XhoI and BamHI sites to pBlunt vector (TransGen Biotech).

PCR3, SphIOch1(274) F (SEQ ID NO: 5, the primer has a Sph I restriction enzyme site) and Och1(+53)XhoI R (SEQ ID NO: 6, the primer has a Xho I restriction enzyme site) primer pair were used for PCR amplification of *Pichia pastoris* OCH1 5' sequence (5'H) using genomic OCH1 gene as a template.

Next, the PCR products of OCH1 5'H was digested with Sph I and Xho I, and pUO3H vector was digested with Xho I and BamH I, respectively. The Sph1-XhoI fragment of OCH1 5'H and XhoI-BamHI fragment of URA3 expression cassette and OCH1 3'H were inserted into the BamH I and Sph I sites of pUC19-EBSH vector. The pUC19-EBSH vector was obtained by replacing pUC19 EcoRI-HindIII fragment of multiple cloning sites with a fragment containing EcoR I, BamH I, Sph I, and Hind III restriction enzyme sites. The yielded pUO vector was used as a basic vector to construct other different OCH1 targeting vectors.

Example 2

Construction of OCH1 Targeting Vector

Figure 3:
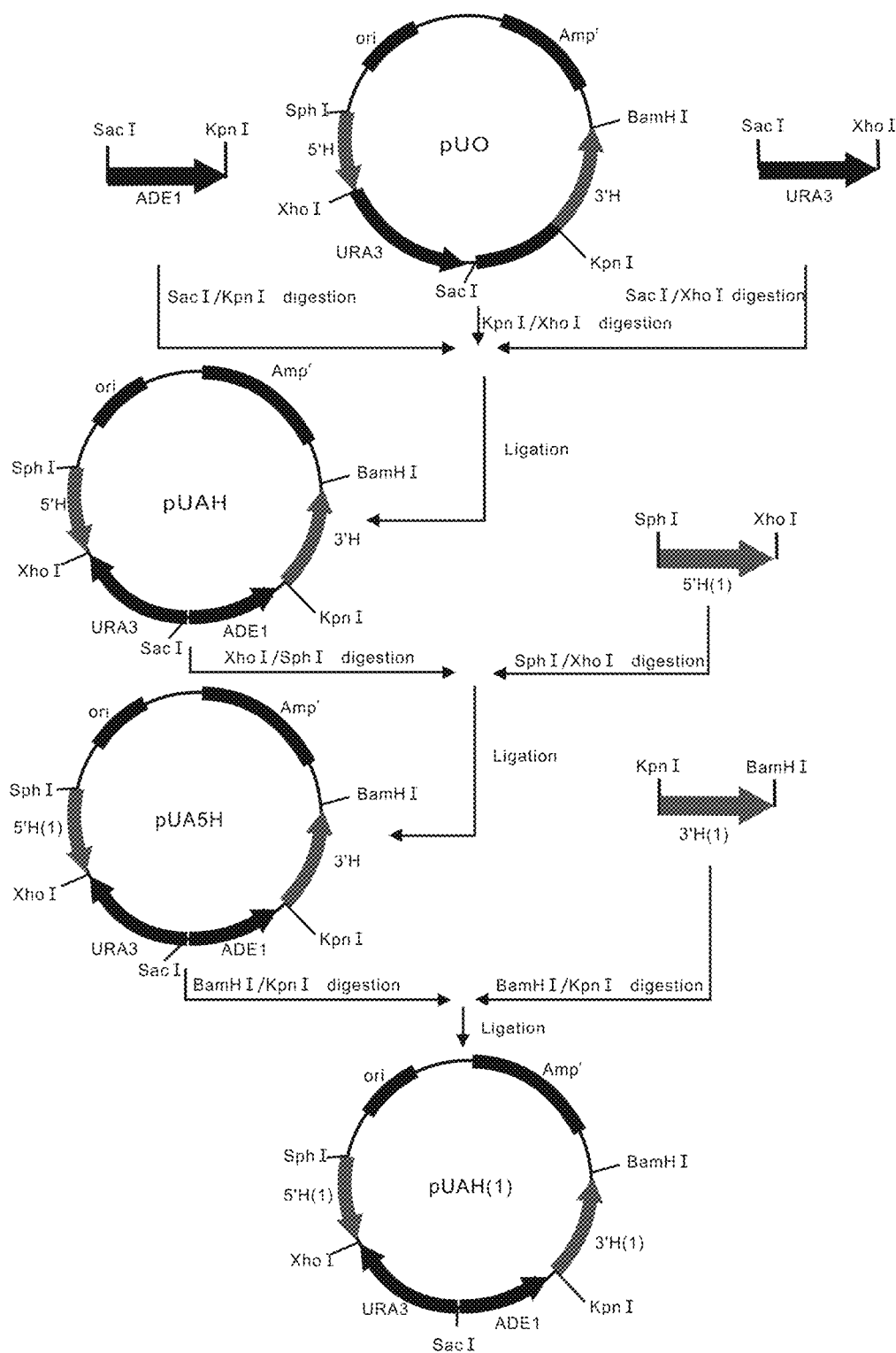
FIG. 3 depicts a scheme to construct a targeting vector of pUAH(1) for integration into the OCH1 locus of *Pichia pastoris*. Vector components are not drawn to scale.

FIG. 3 depicts a scheme to construct a targeting vector for integration into the OCH1 locus of *Pichia pastoris*.

PCR4, SacIADE1 F (SEQ ID NO: 7, the primer has a SacI restriction enzyme site) and ADE1KpnI R (SEQ ID NO: 8, the primer has a KpnI restriction enzyme site) primer pair were used to amplify ADE1 expression cassette using *Pichia pastoris* genomic DNA as a template.

PCR5, SacIURA3 F (SEQ ID NO: 9, the primer has a SacI restriction enzyme site) and URA3XhoI R (SEQ ID NO: 10, the primer has a XhoI restriction enzyme site) primer pair were used to amplify *Pichia pastoris* URA3 expression cassette using pBLURA-SX (Keck Graduate Institute) as a template.

Next, the PCR product of ADE1 expression cassette was digested with SacI and KpnI, and PCR product of URA3 expression cassette was digested with SacI and XhoI, respectively. The SacI-KpnI fragment of ADE1 and SacI-XhoI fragment of URA3 were inserted into the XhoI and KpnI sites of pUO vector to yield pUAH vector.

PCR6, SphIOch1 (−733) F (SEQ ID NO: 11, the primer has a SphI restriction enzyme site) and Och1(−1)XhoI R (SEQ ID NO: 12, the primer has a XhoI restriction enzyme site) primer pair were used for PCR amplification of *Pichia pastoris* OCH1 5' homologous sequence (5'H, −733/−1) using genomic OCH1 gene as a template.

After PCR product digestion with restriction enzymes, SphI-XhoI fragment of OCH1 5' H (−733/−1) was inserted into the same restriction enzyme sites of pUAH to yield an pUA5H.

PCR7, KpnIOch1(1) F (SEQ ID NO: 13, the primer has a KpnI restriction enzyme site) and Och1(646)BamHI R (SEQ ID NO: 14, the primer has a BamHI restriction enzyme site) primer pair were used for PCR amplification of *Pichia pastoris* OCH1 3' homologous sequence (3' H, 1/646) using genomic OCH1 gene as a template.

After PCR product digestion with restriction enzymes, KpnI-BamHI fragment of OCH1 3' H (1/646) were inserted into the same restriction enzyme sites of pUA5H to yield an OCH1 targeting vector pUAH(1), which is used to integrate into the position (−1/1) immediately upstream of start codon in OCH1 5' regulatory region.

In the same way, a series of OCH1 targeting vectors, which integrate at different positions in OCH1 locus, can be constructed by inserting corresponding PCR products of OCH1 5' and 3' homology into pUAH.

A primer pair of SphIOch1 (−118) F (SEQ ID NO: 15) and Och1(553)XhoI R (SEQ ID NO: 16) and a primer pair of KpnIOch1(554) F (SEQ ID NO: 17) and Och1(+103)BamHI R (SEQ ID NO: 18) were used to construct pUAH(554) for integration at the position (553/554) in OCH1 coding region.

A primer pair of SphIOch1(274) F (SEQ ID NO: 19) and Och1(1096)XhoI R (SEQ ID NO: 20) and a primer pair of KpnIOch1(1097) F (SEQ ID NO: 21) and Och1(+801) BamHI R (SEQ ID NO: 22) were used to construct pUAH (1097) for integration at the position (1096/1097) in OCH1 coding region.

A primer pair of SphIOch1(274) F (SEQ ID NO: 19) and Och1(1165)XhoI R (SEQ ID NO: 23) and a primer pair of KpnIOch1(1166) F (SEQ ID NO: 24) and Och1(+801) BamHI R (SEQ ID NO: 22) were used to construct pUAH (1166) for integration at the position (1165/1166) in OCH1 coding region.

A primer pair of SphIOch1(274) F (SEQ ID NO: 19) and Och1(1212)XhoI R (SEQ ID NO: 25) and a primer pair of KpnIOch1 (+1) F (SEQ ID NO: 26) and Och1(+801)BamHI R (SEQ ID NO: 22) were used to construct pUAH(+1) for integration at the position (1212/+1), which immediately upstream of stop codon in OCH1 coding region.

A primer pair of SphIOch1(274) F (SEQ ID NO: 19) and Och1(+3)XhoI R (SEQ ID NO: 27) and a primer pair of KpnIOch1 (+4) F (SEQ ID NO: 28) and Och1(+801)BamHI R (SEQ ID NO: 22) were used to construct pUAH(+4) for integration at the position (+3/+4), which is immediately downstream of stop codon in OCH1 3' regulatory region.

A primer pair of SphIOch1(274) F (SEQ ID NO: 19) and Och1(+203)XhoI R (SEQ ID NO: 29) and a primer pair of KpnIOch1 (+204) F (SEQ ID NO: 30) and Och1(+801) BamHI R (SEQ ID NO: 22) were used to construct pUAH (+204) for integration at the position (+203/+204) in OCH1 3' regulatory region.

A primer pair of SphIOch1(-860) F (SEQ ID NO: 31) and Och1 (-110)XhoI R (SEQ ID NO: 32) and a primer pair of KpnIOch1(-109) F (SEQ ID NO: 33) and Och1(+641) BamHI R (SEQ ID NO: 34) were used to construct pUAH (-109) for integration at the position (-110/-109), which upstream of start codon in OCH1 5' regulatory region.

Example 3

Figure 4A:
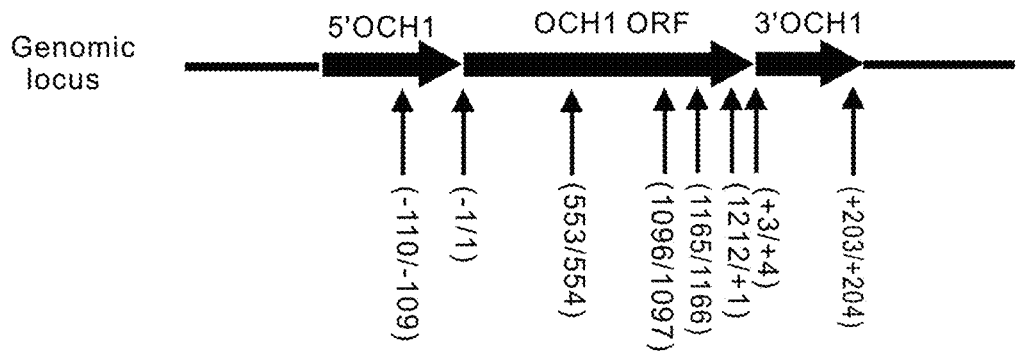
FIG. 4 depicts a scheme of integration at different positions in OCH1 locus in *P. pastoris* genome. Vector components are not drawn to scale. A. diagrams the integration positions of targeting cassette in OCH1 locus of *Pichia pastoris*. The integration positions are indicated by arrows and labeled by the number of the nucleotide at OCH1 locus. Gene components in the vector are not drawn to scale. B. depicts the integration of targeting cassette into the OCH1 locus of *P. pastoris* by double cross-over homologous recombination (knock-in). The cross represents homologous recombination. C. shows PCR verification results for integration at different positions in OCH1 locus. M, DNA size marker; lane 1, wild-type OCH1 in JC301 gives a 1433 bp band with P1/P4 primer pair; lane 2, 3, 4, gene integrations at three positions (−1/1), (1212/+1), and (+3/+4) give no bands, due to over-long sequence (4900 bp) for PCR with P1/P4 primer pair; lane 5, wild-type for OCH1 in JC301 gives no band with P1/P2 primer pair; lane 6, 7, 8. gene integrations at three positions (−1/1), (1212/+1), and (+3/+4)

Targeting Cassettes Integration at Different Positions in OCH1 locus FIG. 4A diagrams the targeting integration positions in OCH1 locus of *Pichia pastoris*. To perform the integration, the series of constructed OCH1 targeting vectors including pUAH (-109, 1, 554, 1097, 1166, +1, +4, and +204) were PCR amplified to generate linear forms of OCH1 targeting cassettes of UAH (-109, 1, 554, 1097, 1166, +1, +4, and +204) with following primer pairs:

Och1(-709) F (SEQ ID NO: 35)/Och1(491) R (SEQ ID NO: 36)
Och1(-600) F (SEQ ID NO: 37)/Och1(600) R (SEQ ID NO: 38)
Och1(-47) F (SEQ ID NO: 39)/Och1(1153) R (SEQ ID NO: 40)
Och1(496) F (SEQ ID NO: 41)/Och1(+484) R (SEQ ID NO: 42)
Och1(565) F (SEQ ID NO: 43)/Och1(+553) R (SEQ ID NO: 44)
Och1(612) F (SEQ ID NO: 45)/Och1(+600) R (SEQ ID NO: 46)
Och1(615) F (SEQ ID NO: 47)/Och1(+603) R (SEQ ID NO: 48)
Och1(816) F (SEQ ID NO: 49)/Och1(+803) R (SEQ ID NO: 50).

OCH1 targeting cassettes contain URA3 and ADE1 expression cassettes, which are located adjacent to each other on opposite strands and in opposite orientations. Both expression cassettes are flanked by the 5' and 3' integrating homology sequences (5'H and 3'H) at the same length of 600 bp, which are locus-specific homologous sequences to guarantee a precise integration at the targeting positions in OCH1 locus.

The targeting cassettes were transformed into the cells of *P. pastoris* auxotrophic strains JC301 (ade1 his4 ura3) (Keck Graduate Institute) by electroporation with MicroPulser™ electroporation apparatus following manufacturer (BioRad, USA) operating instructions. The transformed cells were grown on YNB plates supplemented with 20 mg/L histidine to select for adenine and uracil prototrophy.

Figure 4B:
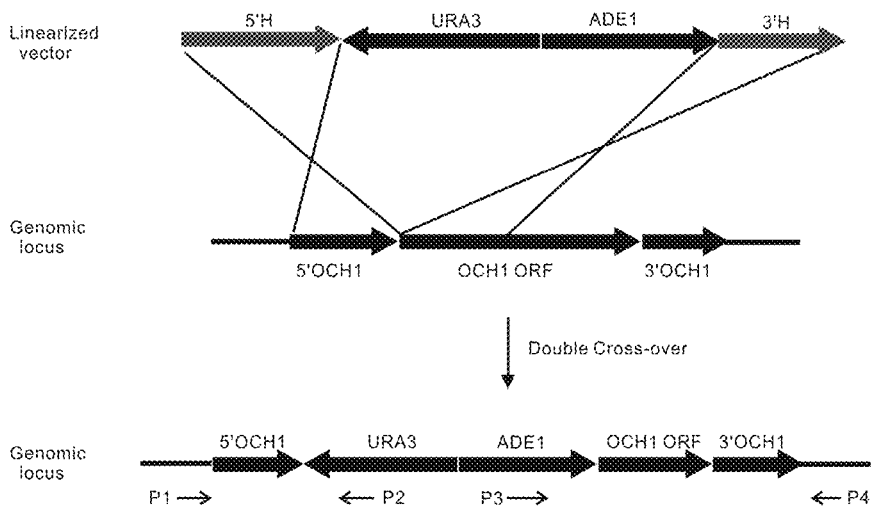
Figure 4C:
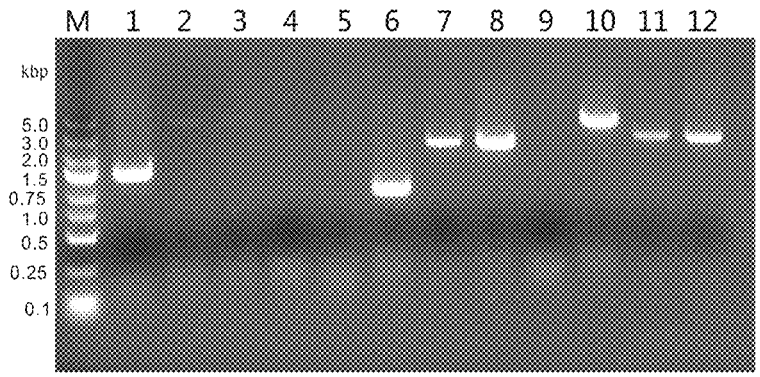

FIG. 4B depicts a representative homologous integration of a targeting cassette at the position (-1/1) immediately upstream the start codon of OCH1 locus in *Pichia pastoris*. In each plate of transformation, colonies were randomly picked and cultured to extract genomic DNA for PCR verification of genomic integration. Two primer pairs, P1 (SEQ ID NO: 51, located upstream of the 5' homologous region in the genome)/P2 (SEQ ID NO: 52, located within URA3 of targeting fragment) and P3 (SEQ ID NO: 53, located within ADE1 of targeting fragment)/P4 (SEQ ID NO: 54, located downstream of the 3' homologous region in the genome), were used to verify homologous integration at the targeting position (FIG. 4B). FIG. 4C shows PCR verification results for integration at different positions in OCH1 locus. The expected 1300, 2550, and 2550 bp bands were amplified by the P1/P2 primer pair, respectively. These strains also revealed the expected 3500, 2300, and 2300 kb bands by using P3/P4 primer pair in PCR. PCR results verified that corresponding targeting fragments were successfully integrated at the specified positions (-1/1, 1212/+1, +3/+4), respectively. As a negative control of the parent strain JC301, 1433 bp band was amplified by P1/P4 primer pairs, but no band was amplified by P1/P2 and P3/P4 primer pairs, respectively. The strain of integration at immediately upstream of start codon in OCH1 locus is named as och1 (-1/+1, ADE1URA3) strain.

In this example, it demonstrates the significant different efficiencies of homologous recombination integration at different positions in OCH1 locus, when the same length of 600 bp homology sequence is used (Table 1). The integration transformants, which have integration at these positions (553/554, 1096/1097, and 1165/1166) in coding region, can not be identified among 100 screened colonies. Since integration at OCH1 coding region leads to disruption of OCH1 gene function and lose of cellular fitness, homologous integrations are not the preferred mechanism for disruptions of OCH1 coding region in genome. Instead, targeting cassettes are integrated into the genome randomly through non-homologous end joining. It is consistent with previous reports that the disruption of OCH1 in *P. pastoris* is significantly low efficient at a frequency of 0.1%, but difficult to obtain the same result by other laboratories, when~1 kb or more regions of homology are used (Choi, 2003, Proc Natl Acad Sci USA 100: 5022-5027; Chen, 2013, PLoS ONE 8(3): e57952).

It is well known that *Pichia pastoris* has very low efficiencies in HR gene targeting. The frequency of gene replacement events is highly dependent on the length of the targeting fragments. The frequency can be less than 0.1% when the targeting homologous sequences are less than 500 bp.

However, on the contrary to previous reports, this invention found that homologous integration at the position (1212/+1) immediately upstream stop codon is at a frequency of ~7%, when a short 600 bp regions of homology were used. This could be attributed to the incompletely disruption of OCH1 function, because the integration leads to nonstop mRNA for C-terminal extended OCH1 product with some functional activity. It is expected that homologous integration frequencies at the sites proximal to 3' end of ORF is higher than that at the sites in other ORF region, as long as the forming C-terminal extended products keep some activity.

In addition, this invention also found that there are remarkable high frequencies of homologous integration at the positions in OCH1 5'- and 3'-regulatory region, such as 40%, 35% at the positions (-110/-109, -1/1) upstream start codon, and 80%, 25% at two positions (+3/+4, +203/+204) downstream of stop codon, respectively.

Example 4

Targeting Cassettes Integration at Different Positions in ADE1 Locus

The efficiency of targeting integration at different positions in ADE1 locus was performed to further verify the results from OCH1 gene targeting.

Figure 5A:
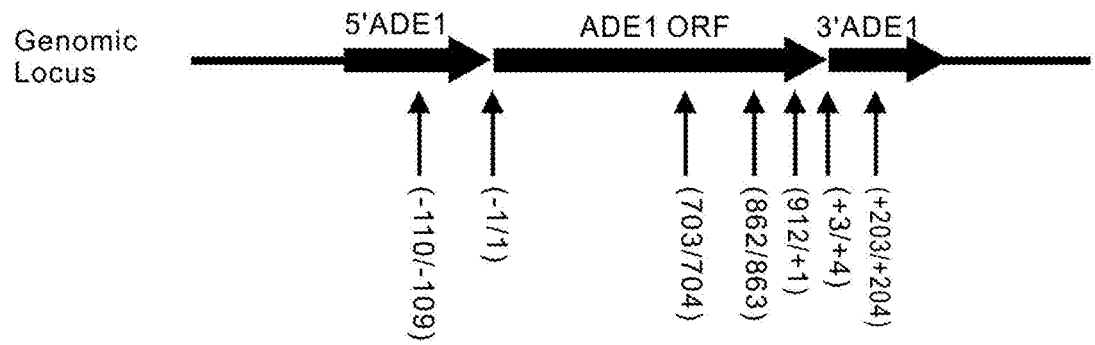

FIG. 5A diagrams the integration positions of targeting cassettes in genomic ADE1 locus.

Figure 5B:
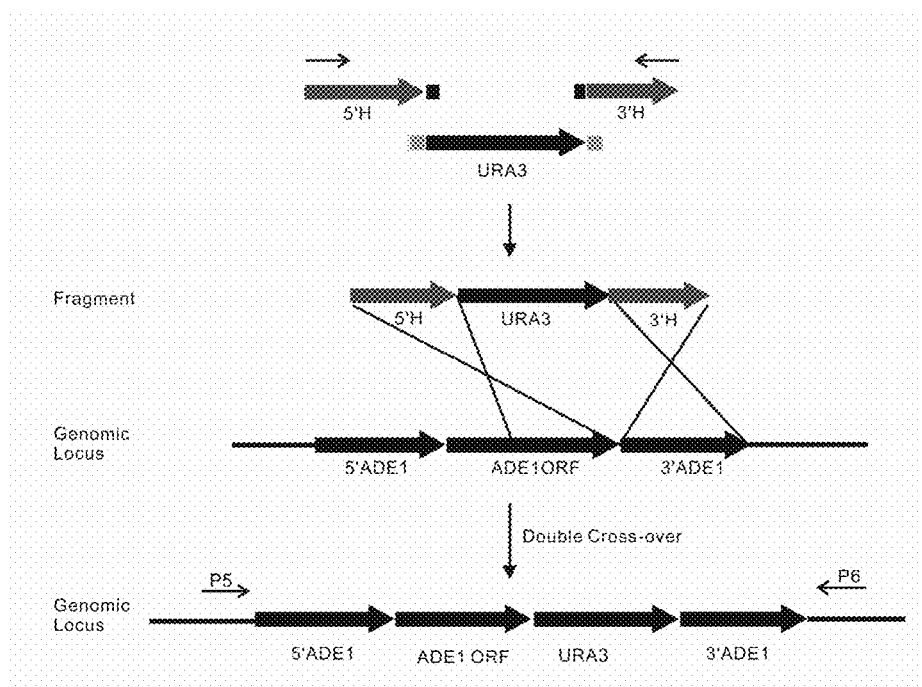

FIG. 5B shows a scheme to construct ADE1 targeting cassettes by PCR

PCR1, ADE1(-800) F (SEQ ID NO: 55) and ADE1(-1)U R (SEQ ID NO: 56, the primer has URA3 overlapping sequence for fusion PCR) primer pair were used for PCR amplification of 5'-homologous sequence (5'H, -800/-1) using genomic ADE1 gene as a template.

PCR2, primer pair of A(-21)URA3 F (SEQ ID NO: 57) and URA3A(19) R (SEQ ID NO: 58, both have ADE1 overlapping sequence for fusion PCR) were used for amplification of URA3 expression cassette using pBLURA-SX vector as a template.

PCR3, UADE1(1) F (SEQ ID NO: 59, the primer has URA3 overlapping sequence for fusion PCR) and ADE1(800) R (SEQ ID NO: 60) primer pair were used for PCR amplification of 3'-homologous sequence (3'H, 1/800) using genomic ADE1 gene as a template.

The above three PCR products (1, 2, 3) were joined by overlap-extension PCR using ADE1(-800) F (SEQ ID NO: 55) and ADE1(800) (SEQ ID NO: 60) primer pair. This yielded a linear targeting cassette UH (1), which integrates at the position (-1/1) immediately upstream of start codon in ADE1 5' regulatory region.

In the same way, a series of ADE1 targeting cassettes, which integrate at different positions in ADE1 locus, can be constructed by PCR amplification and fusion using following corresponding primer pairs:

Primer pair of ADE1(-98) F (SEQ ID NO: 61) and ADE1(703)U R (SEQ ID NO: 62, It has URA3 overlapping sequence for fusion PCR), primer pair of A(684)URA3 F (SEQ ID NO: 63) and URA3A(728) R (SEQ ID NO: 64, Both have ADE1 overlapping sequence for fusion PCR), and primer pair of ADE1(704) F (SEQ ID NO: 65, It has URA3 overlapping sequence for fusion PCR) and ADE1(+591) R (SEQ ID NO: 66) were used to construct targeting cassette UH(704) for integration at the position (703/704) in ADE1 coding region. Primer pair of ADE1(62) F (SEQ ID NO: 67) and ADE1(862)U R (SEQ ID NO: 68, It has URA3 overlapping sequence for fusion PCR), primer pair of A(842) URA3 F (SEQ ID NO: 69) and URA3A(881) R (SEQ ID NO: 70, Both have ADE1 overlapping sequence for fusion PCR), and primer pair of UADE1(863) F (SEQ ID NO: 71, It has URA3 overlapping sequence for fusion PCR) and ADE1(+750) R (SEQ ID NO: 72) were used to construct targeting cassette UH(863) for integration at the position (862/863) in ADE1 coding region.

Primer pair of ADE1(62) F (SEQ ID NO: 67) and ADE1(912)U R (SEQ ID NO: 73, It has URA3 overlapping sequence for fusion PCR), primer pair of A(896)URA3 F (SEQ ID NO: 74) and URA3A(+21) R (SEQ ID NO: 75, Both have ADE1 overlapping sequence for fusion PCR), and primer pair of UADE1(+1) F (SEQ ID NO: 76, It has URA3 overlapping sequence for fusion PCR) and ADE1(+750) R (SEQ ID NO: 72) were used to construct targeting cassette UH(+1) for integration at the position (912/+1) immediately upstream of ADE1 stop codon in coding region.

Primer pair of ADE1(62) F (SEQ ID NO: 67) and ADE1(+3)U R (SEQ ID NO: 77, It has URA3 overlapping sequence for fusion PCR), primer pair of A(896)URA3 F (SEQ ID NO: 78) and URA3A(+23) R (SEQ ID NO: 79, Both have ADE1 overlapping sequence for fusion PCR), and primer pair of UADE1(+4) F (SEQ ID NO: 80, It has URA3 overlapping sequence for fusion PCR) and ADE1(+750) R (SEQ ID NO: 72) were used to construct targeting cassette UH(+4) for integration at the position (+3/+4) immediately downstream of ADE1 stop codon in 3' regulatory region.

Primer pair of ADE1(298) F (SEQ ID NO: 81) and ADE1(+203)U R (SEQ ID NO: 82, It has URA3 overlapping sequence for fusion PCR), primer pair of A(+186)URA3 F (SEQ ID NO: 83) and URA3A(+226) R (SEQ ID NO: 84, Both have ADE1 overlapping sequence for fusion PCR), and primer pair of ADE1(+204) F (SEQ ID NO: 85, It has URA3 overlapping sequence for fusion PCR) and ADE1(+1004) R (SEQ ID NO: 86) were used to construct targeting cassette UH(+204) for integration at the position (+203/+204) in ADE1 3' regulatory region.

Primer pair of ADE1(-895) F (SEQ ID NO: 87) and ADE1(-110)U R (SEQ ID NO: 88, It has URA3 overlapping sequence for fusion PCR), primer pair of A(-133)URA3 F (SEQ ID NO: 89) and URA3A(-87) R (SEQ ID NO: 90, Both have ADE1 overlapping sequence for fusion PCR), and primer pair of UADE1(-109) F (SEQ ID NO: 91, It has URA3 overlapping sequence for fusion PCR) and ADE1(691) R (SEQ ID NO: 92) were used to construct targeting cassette UH(-109) for integration at the position (-110/-109) upstream of ADE1 start codon in 5' regulatory region.

These linear targeting cassettes contain URA3 expression gene, which are flanked on both sides by 5' and 3' homologies at the similar length around 800 bp (750-850), which are locus-specific homologous sequences for precise integration at the targeting positions in ADE1 locus of *Pichia pastoris*.

These targeting cassettes were transformed into the cells of *P. pastoris* auxotrophic strains JC307 (his4 ura3) (Keck Graduate Institute, USA) by electroporation. The transformed cells were grown on SC plate (8 g/L SC without histidine and uracil, 20 g/L dextrose, 15 g/L agar) supplemented with 20 mg/L histidine and to select for uracil prototrophy. Colonies were randomly picked from the plate in 2-3 days incubation to avoid the bias between white/pink colonies, since the accumulation of a red pigment and appearance of pink colonies in ade1 strains require longer incubation. Genomic DNAs were extracted from overnight cultured colonies and used to verify the integration at the positions in ADE1 locus by PCR.

Figure 5C:
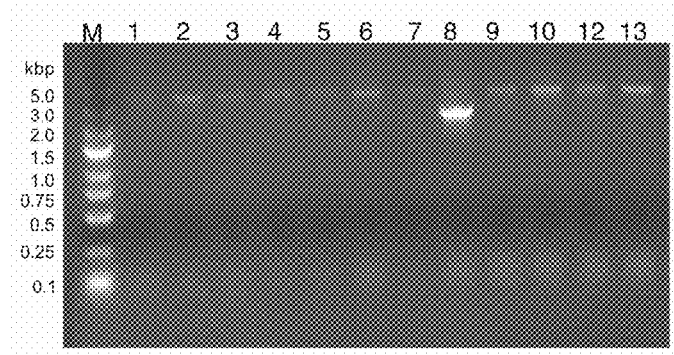

Primer pair of P5/P6 (located upstream of the 5' homologous region, and downstream of the 3' homologous region in the genome) were used to verify genome integration (FIG. 5B). The corresponding P5/P6 primer pair is further named as P5-1 (SEQ ID NO: 93)/P6-1 (SEQ ID NO: 94), P5-2 (SEQ ID NO: 95)/P6-2 (SEQ ID NO: 96), P5-3 (SEQ ID NO: 97)/P6-3 (SEQ ID NO: 98) and P5-4 (SEQ ID NO: 99)/P6-4 (SEQ ID NO: 100) to verify the integrations at different positions in ADE1 locus. For example, the successful amplification of a band with the expected size of 3763 bp indicated that the chromosomal integrations at 912/+1 position were correct, but the amplification of a band with the size of 2398 bp indicated no chromosomal integration (FIG. 5C).

In this example, it also demonstrates the significant difference of HR integration efficiencies at different sites of ADE1 locus, when the similar length around 800 bp homology is used (Table 1). Integrations at the positions (862/863, and 912/+1) proximal to the 3' end of ORF were at frequencies over 15%, but integration at the position (703/704) in the middle ORF is only at a frequency of 3%. Like OCH1 integration, it also suggests that integration at the sites proximal to 3' end of ORF is easier than in other ORF region.

In consistent with OCH1 integration results, there are significant high frequencies of homologous integration at the positions in ADE1 5'- and 3'-regulatory region, such as 50%, 65% at the position (−110/−109, −1/1) immediately upstream start codon, and 30%, 45% at two positions (+3/+4, +203/+204) downstream of stop codon, respectively.

Previous reports indicate that the frequency of HR gene targeting is locus dependent, such as OCH1 locus has extremely low efficiency and ADE1 locus has high frequency. However, this invention found that the frequency of HR gene targeting is mainly dependent on the regions of the target locus. Although there are completely different frequencies for HR integrations in OCH1 and ADE1 ORF to disrupt their function, there are high efficiencies at frequencies over 25% for gene integrations at the 5' and 3' region of both OCH1 and ADE1 loci, when less than 1 kb homology is used. This invention found that the frequency of HR gene integration at 5'- and 3'-regulatory regions is locus independent and is at significant high efficiency. In addition, the frequency of gene integration at the sites proximal to 3' end of ORF is higher than at other sites of ORF. The frequency of HR targeting integration in different regions of genome locus can be expressed in following order: 5'-regulatory region and 3'-regulatory region>>3' end of coding region>other coding region. These findings in the present invention provide new opportunities to regulate the target gene function.

Example 5

Gene Integration to Regulate the Activity of β-Galactosidase.

Gene targeting on OCH1 and ADE1 has identified the high efficient integration positions at 5' and 3' regulatory region. However, no systematic analysis has been performed to correlate the effect of integration positions at 5' and 3' regulatory region with gene transcription and protein expression levels.

The lacZ gene of *Escherichia coli* encodes the enzyme β-galactosidase, which hydrolyzes a variety of β-D-galactosides including chromogenic substrates to yield a colored product. Because of the ease and sensitivity of its activity assay in liquid culture, β-galactosidase is a common use report enzyme to monitor the regulation of gene expression. The lacZ reporter in *P. pastoris* can be constructed by fusing lacZ ORF to 5' and 3' regulatory region of a gene.

(1) Construction of 5'AOX1-Induced lacZ Expression Vectors

FIGS. 6 and 7 depict the scheme to construct a series of 5'AOX1-induced lacZ expression vectors, in which URA3 is positioned next to start and stop codons in lacZ ORF to regulate its expression.

PCR1, BamHIlacZ F (SEQ ID NO: 101, The primer has a BamHI restriction enzyme site) and lacZNotI R (SEQ ID NO: 102, Ther primer has NotI and XhoI restriction enzyme sites) primer pair was used for PCR amplification of lacZ ORF (SEQ ID NO: 128) using *E. Coli* BL21(DE3) genomic lacZ DNA as a template.

PCR2, BamHIlacZ F (SEQ ID NO: 101) and lacZnsNotI R (SEQ ID NO: 103, The primer lacks lacZ stop codon and has NotI and XhoI restriction enzyme sites) primer pair was used in PCR to amplify *E. coli* lacZ ORF using *E. Coli* BL21(DE3) genomic DNA as a template.

Next, the PCR products of lacZ and lacZns were digested with BamHI and NotI. The digested BamHI/NotI. fragments of lacZ and lacZns were inserted into the BamHI and NotI sites of pPIC3.5K vector (Invitrogen) to yield p5'AOX1-lacZ and p5'AOX1-lacZns vectors (FIG. 6).

PCR3, BamHIURA3 F (SEQ ID NO: 104, The primer has a BamHI restriction enzyme site) and URA3BamHI R (SEQ ID NO: 105, The primer has a BamHI restriction enzyme site) primer pair was used in PCR to amplify *P. pastoris* URA3 expression cassette using pBLURA-SX vector as a template.

The PCR product of URA3 expression cassette was digested with BamHI, and inserted into the BamHI site of p5'AOX1-lacZ vector. The ligated vectors containing URA3 at both orientations were transformed into *E. coli* strain Trans1-T1 (TransGen Biotech, China), and colony PCR was performed to select vector p5'AOX1-URA3-lacZ, in which URA3 is located immediately upstream of lac ORF at the same strand and orientation (FIG. 6).

PCR4, NotIURA3 F (SEQ ID NO: 106, The primer has a NotI restriction enzyme site) and URA3NotI R (SEQ ID NO: 107, The primer has a NotI restriction enzyme site) primer pair was used in PCR to amplify *P. pastoris* URA3 expression cassette using pBLURA-SX vector as a template.

The PCR product of URA3 expression cassette was digested with NotI, and inserted into the NotI site of p5'AOX1-lacZ and p5'AOX1-lacZns vectors, respectively. The ligated vectors containing URA3 at both orientations were transformed into Trans1-T1 Phage Resistant, and colony PCR was performed to individually select vectors of p5'AOX1-lacZ-URA3, p5'AOX1-lacZ-URA(−) and p5'AOX1-lacZns-URA3, p5'AOX1-lacZns-URA3(−). Both p5'AOX1-lacZ-URA3 and p5'AOX1-lacZns-URA3 contain URA3 expression cassette, which is located immediately downstream of lac ORF and lacZns ORF at the same strand and orientation (FIG. 6). Another two vectors p5'AOX1-lacZ-URA3(−) and p5'AOX1-lacZns-URA3(−) contain URA3 expression cassette, which is located immediately downstream of lac ORF and lacZns ORF at the opposite strand and opposite orientation (FIG. 7).

(2) Construction of 5'OCH1-Mediated lacZ Expression Vectors

FIGS. 8, 9, 10 and 11 depict the scheme to construct a series of 5'OCH1-mediated lacZ expression vectors, in which URA3 is positioned next to start and stop codons in lacZ ORF to regulate its expression.

PCR1, BamHIOCH1(−731) F (SEQ ID NO: 108, The primer has a BamHI restriction enzyme site) and OCH1(−1)L R (SEQ ID NO: 109, The primer has lacZ overlapping sequence for fusion PCR) primer pair were used in PCR to amplify 5' regulatory region of OCH1 (5'OCH1, −731/−1) using genomic DNA as a template.

PCR2, OLacZ F (SEQ ID NO: 110, The primer has 5'OCH1 overlapping sequence for fusion PCR) and lacZXhoI R (SEQ ID NO: 111, The primer has XhoI restriction enzyme site) primer pair were used in PCR to amplify lacZ ORF using *E. Coli* BL21(DE3) genomic DNA as a template.

PCR3, OLacZ F (SEQ ID NO: 110) and lacZnsNotI R (SEQ ID NO: 103, The primer lacks lacZ stop codon and has NotI and XhoI restriction enzyme sites) primer pair were used in PCR to amplify lacZ ORF without stop codon (lacZns) using *E. Coli* BL21(DE3) genomic DNA as a template.

PCR4, the PCR1 and 2 products were fused by overlap-extension PCR using BamHIOCH1(−731) F (SEQ ID NO: 108) and LacZXhoI R (SEQ ID NO: 111) primer pair. This yielded a fragment of 5'OCH1-lacZ.

PCR5, the PCR1 and 3 products were fused by overlap-extension PCR using BamHIOCH1(−731) F (SEQ ID NO: 108) and lacZnsNotI R (SEQ ID NO: 103) primer pair. This yielded a fragment of 5'OCH1-lacZns.

PCR6, XhoIOCH1(+4) F (SEQ ID NO: 112, The primer has XhoI restriction enzyme site) and OCH1(+798)SacI R (SEQ ID NO: 113, The primer has SacI restriction enzyme site) primer pair were used in PCR to amplify 3' regulatory region of OCH1 (3'OCH1, +4/+798) using genomic DNA as a template.

Next, the PCR product of 5'OCH1-lacZ fragment was digested with BamHI and XhoI, and PCR product of 3'OCH1 was digested with XhoI and SacI, respectively. The BamHI-XhoI fragment of 5'OCH1-lacZ and XhoI-SacI fragment of 3'OCH1 were inserted into the SacI and BamHI sites of pBLHIS-SX vector to yield p5'OCH1-lacZ vector (FIG. 8).

And, the PCR product of 5'OCH1-lacZns fragment was digested with BamHI and XhoI, and PCR product of 3'OCH1 was digested with XhoI and SacI, respectively. The BamHI-XhoI fragment of 5'OCH1-lacZns and XhoI-SacI fragment of 3'OCH1 were inserted into the SacI and BamHI sites of pBLHIS-SX vector to yield p5'OCH1-lacZns vector (FIG. 8).

PCR7, BamHIOCH1(−731) F (SEQ ID NO: 108) and OCH1(−1)U R (SEQ ID NO: 114, The primer has URA3 overlapping sequence for fusion PCR) primer pair were used in PCR to amplify 5' regulatory region of OCH1 (5'OCH1, −731/−1) using genomic DNA as a template.

PCR8, OURA3 F (SEQ ID NO: 115, The primer has OCH1 overlapping sequence for fusion PCR) and URA3SphIXhoI R (SEQ ID NO: 116, The primer has SphI and XhoI restriction enzyme sites) primer pair were used in PCR to amplify P. pastoris URA3 expression cassette using pBLURA-SX vector as a template.

PCR9, the PCR7 and 8 products were fused by overlap-extension PCR using BamHIOCH1(−731) F (SEQ ID NO: 108) and URA3SphIXhoI R primer pair (SEQ ID NO: 116). This yielded a fragment of 5'OCH1-URA3.

PCR10, SphILacZ F (SEQ ID NO: 117, The primer has SphI restriction enzyme site) and LacZXhoI R (SEQ ID NO: 111) primer pair were used in PCR to amplify lacZ ORF using E. Coli BL21(DE3) genomic DNA as a template.

Next, the PCR product of 5'OCH1-URA3 fragment was digested with BamHI and XhoI, and the PCR product of lacZ ORF was digested with SphI and XhoI, respectively. The BamHI-XhoI fragment of 5'OCH1-URA3 and SphI-XhoI fragment of lacZ were inserted into the BamHI and XhoI sites of p5'OCH1-lacZ vector to yield p5'OCH1-URA3-lacZ vector (FIG. 9).

PCR11, XhoIURA3 F (SEQ ID NO: 3, The primer has XhoI restriction enzyme site) and URA3XhoI R (SEQ ID NO: 10, The primer has a XhoI restriction enzyme site) primer pair were used in PCR to amplify P. pastoris URA3 expression cassette using pBLURA-SX vector as a template.

The PCR product of URA3 expression cassette was digested with XhoI, and inserted into the XhoI site of p5'OCH1-lacZ and p5'OCH1-lacZns vectors, respectively. The insertion vectors containing URA3 at both orientations were transformed into Trans1-T1 strains, and colony PCR was performed to individually select the vectors of p5'OCH1-lacZ-URA3, p5'AOX1-lacZ-URA(−) and p5'OCH1-lacZns-URA3, p5'OCH1-lacZns-URA3(−). Both p5'OCH1-lacZ-URA3 and p5'OCH1-lacZns-URA3 contain URA3 expression cassette, which is located immediately downstream of lacZ ORF and lacZns ORF at the same strand and orientation. Another two vectors p5'OCH1-lacZ-URA3 (−) and p5'OCH1-lacZns-URA3(−) contain URA3 expression cassette, which is located immediately downstream of lacz ORF and lacZns ORF at the opposite strand and opposite orientation (FIGS. 10 and 11).

(3) Transformation of lacZ Expression Vectors

5'AOX1-induced lacZ expression vectors, including p5'AOX1-lacZ, p5'AOX1-URA3-lacZ, p5'AOX1-lacZ-URA3, p5'AOX1-lacZ-URA3(−), p5'AOX1-lacZns-URA3, and p5'AOX1-lacZns-URA3(−), were linearized with SacI digestion, and transformed in P. pichia strain GS115 (his4) (Invitrogen) by electroporation. Transformed cells were grown on YNB plate to select for histidine prototrophy. The linearized expression vectors were integrated at genome by single cross (roll-in) recombination as described by manufacturer (Invitrogen).

5'OCH1-mediated lacZ expression vectors, including p5'OCH1-lacZ, p5'OCH1-URA3-lacZ, p5'AOX1-lacZ-URA3, p5'AOX1-lacZns-URA3(−), p5'AOX1-lacZns-URA3, and p5'AOX1-lacZ-URA3(−), were linearized with stu I digestion, and transformed in P. pichia strain GS115 by electroporation. The transformed cells were grown on YNB plates to select for histidine prototrophy. The linearized expression vectors were integrated at his4 locus by single cross (roll-in) recombination.

(4) Real-Time PCR Analysis of lacZ mRNA

The transformed cells, which contain 5'AOX1-induced lacZ expression vectors, were grown in 5 ml BMGY medium (10 g/L yeast extract, 20 g/L peptone, 13.4 g/L YNB without amino acids, 100 mM potassium phosphate buffer, pH 6.0, 0.4 mg/L biotin, 10 ml/L glycerol) at 30° C. and 225 rpm shaking for 48 hours. Cells were pelleted by centrifugation at 3000 g for 5 minutes and resuspended in 5 ml BMMY medium (10 g/L yeast extract, 20 g/L peptone, 13.4 g/L YNB without amino acids, 100 mM potassium phosphate buffer, pH 6.0, 0.4 mg/L biotin, 10 ml/L methanol) at 30° C. and 225 rpm to induce lacZ expression. Induction was maintained for another 48 hours by spiking the cultures twice daily with 50 µl of 100% methanol (1% final concentration). Subsequently, cells were centrifuged at 3000 g for 10 minutes, washed in 5 ml of water, re-centrifuged to collect cell pellets. Cell pellets were used for β-galactosidase assay and stored at −80° C. for total RNA isolation.

The transformed cells, which contain 5'OCH1-mediated lacZ expression vectors, were grown in 5 ml YPD medium at 30° C. and 225 rpm shaking for 72 hours. Subsequently, cells were centrifuged at 3000 g for 10 minutes, washed in 5 ml of water, re-centrifuged to collect cell pellets. Cell pellets were used for β-galactosidase assay and stored at −80° C. for total RNA isolation.

Total RNA isolation was performed by using TRIzol® Reagent (Lifetechnologies) according to the manufacturer's instructions.

Reverse transcription of RNA was carried out with the ReverTra Ace-α-First strand cDNA Synthesis kit (Toyobo) according to the manufacturer's instructions.

Real-time PCR reactions were composed of 10 µL of 2×iTaq™ Universal SYBR® Green supermix (BioRad, Hercules, Calif.), 1 µl of cDNA, and 100 nM each of GAPDH F/R and LacZ F/R primers in a 20 µL total reaction volume. PCR reactions were carried out in LightCycler LC480 (Roche) with the following parameters (1 cycle of 95° C. for 1 min, 40 cycles of 95° C. for 10 sec, 58° C. for 10 sec, 72° C. for 10 sec). All samples were performed in triplicate and tested several times. Manufacture (Roche) software was utilized to analyze real-time PCR data. The relative expression of mRNA is determined with the comparative $C_T$ method ($\Delta\Delta C_T$ method). Glyceraldehyde-3-phosphate dehydrogenase was used as an endogenous control for the quantification of gene expression.

FIGS. 12A and B show the inhibition effect on 5'AOX1 and 5'OCH1 initiated lacZ mRNA expression, as URA3 expression cassette is integrated next to start and stop codon. As URA3 expression cassette is integrated immediately upstream the start codon of lacZ ORF in the same strand and orientation, it efficiently reduced lacZ mRNA levels by 60% and 70%, respectively. This mRNA reducing can be attributed to 3' URA3 terminator, which is located upstream of lacZ ORF and blocks lacZ transcription initiated by 5'AOX1 or 5' URA3 promoter. The leakage of termination may yield the low level of aberrant lacZ mRNA, which lacks proper 5'UTR for translation.

As URA3 expression cassette was integrated immediately upstream the stop codon of lacZ ORF in two strands at two orientations, it was expected to yield aberrant lacZ mRNA lacking a stop codon (nonstop lacZ mRNA, lacZns). As URA3 expression cassette was integrated at the position immediately downstream the stop codon of lacZ ORF in two strands at two orientations, it was expected to yield lacZ mRNA containing aberrant 3'UTR. RT-PCR analysis has shown that integrations around the stop codon can either increase or decrease lacZ aberrant mRNA levels initiated by 5'AOX1 or 5'OCH1 (FIGS. 12A and B). These results are different from previous report that cells have surveillance systems to recognize and eliminate aberrant mRNAs to avoid the potentially harmful protein products (van Hoof A, Frischmeyer P A, Dietz H C, Parker R (2002) Exosome mediated recognition and degradation of mRNAs lacking a termination codon. Science 295: 2262-2264). Therefore, integrations around stop codon in both strands and orientations have to be evaluated to obtain optimal effect in regulating the target gene transcription.

(5) Assay for β-Galactosidase Activity

To further access the inhibition effect of integration of URA3 expression cassette on 5'AOX1 and 5'OCH1 mediated protein expression, the intracellular specific activities of β-galactosidase in collected cell pellets were measured using standard protocols (Ausubel F M et al. Current Protocols in Molecular Biology, Wiley InterScience, 2010).

FIGS. 13A and B show the relative intracellular specific activities of β-galactosidase in responding to gene integration of URA3 expression cassette around start and stop codons. There was no detectable β-galactosidase activity in cells, as URA3 integration was at the position immediately upstream the start codon of lacZ ORF in the same strand and orientation. The complete suppression of β-galactosidase activity can be attributed to both transcription and translation regulation effects. Firstly, the termination effect of 3' URA3 significantly reduced transcription of aberrant lacZ mRNA, which lacks 5'UTR. Secondly, translation can not be initiated in aberrant lacZ mRNA without proper 5'UTR.

The present invention demonstrates that gene integration at 5' regulatory region, especially at position immediately upstream of ORF, can specifically suppress a target gene expression by interrupting both transcription and translation. At present, the methods of regulating gene transcription mainly include: altering template function by inhibiting the binding of molecules to DNA, and inhibit transcriptional activity by inhibiting the binding of molecules to RNA polymerase. The method of regulating protein translation mainly uses small RNA binding to RNA-binding protein and mRNA to change its translation ability. However, these methods are not specific to the regulation of target gene expression. In contrast, gene integration in genomic genes, particularly upstream of ORF, is a more effective way for specifically controlling target gene expression.

As URA3 integration had different effect in lacZ aberrant mRNA levels, URA3 integration around stop codon in different strands and orientations had various inhibition effects on 5'AOX1 and 5'OCH1 mediated translation of β-galactosidase in cells. The β-galactosidase activity can be reduced up to 70% when URA3 was integrated around stop codon in proper orientation. This suppression effect is more efficient than previous reported inhibition by microRNAs. It is reported that microRNAs are associated with repression of 32% and 4% at mRNA stability and translational levels, respectively (Noah Spies, Christopher B. Burge, and David P. Bartel (2013). 3' UTR-isoform choice has limited influence on the stability and translational efficiency of most mRNAs in mouse fibroblasts, Genome Research, 23:2078-2090).

This invention illustrates another method to control target gene expression by integration around stop codon. Gene integrations in both strands and orientations around stop codon have to be evaluated to get optimal regulation result.

Example 6

Gene Integration to Suppress OCH1 Expression.

To further access the effect of gene integration to regulate genomic gene transcription, representative integration strains in Example 3 were selected to analysis mRNA transcription of OCH1 locus. Cells of control strain JC307 and three integration strains, och1(−1/+1), (1212/+1), (+3/+4), were grown in 5 ml YPD medium at 30° C. and 225 rpm shaking for 72 hours. Subsequently, cells were centrifuged at 3000 g for 10 minutes, washed in 5 ml of water, re-centrifuged to collect cell pellets and stored at −80° C. for subsequent total RNA isolation.

Total RNA was isolated by using TRIzol® Reagent (Lifetechnologies), and reverse transcribed to cDNA with the ReverTra Ace-α-First strand cDNA Synthesis kit (Toyobo).

Real-time PCR reactions were composed of 10 μL of 2×iTaq™ Universal SYBR® Green supermix (BioRad, Hercules, Calif.), 1 μl of cDNA, and 100 nM each of GAPDH F(SEQ ID NO: 118)/R (SEQ ID NO: 119) and OCH1 F (SEQ ID NO: 122)/R (SEQ ID NO: 123) primers in a 20 μL total reaction volume. PCR reactions were carried out in LightCycler LC480 (Roche) with the following parameters (1 cycle of 95° C. for 1 min, 40 cycles of 95° C. for 10 sec, 58° C. for 10 sec, 72° C. for 10 sec). All samples were performed in triplicate and tested several times. Manufacture (Roche) software was utilized to analyze real-time PCR data. The relative expression of mRNA is determined with the comparative $C_T$ method ($\Delta\Delta C_T$ method). Glyceraldehyde-3-phosphate dehydrogenase (GAPDH) was used as an endogenous control for the quantification of gene expression.

FIG. 14 shows relative OCH1 mRNA expression in these strains. Gene integration at the position upstream the start codon can effectively suppress the OCH1 mRNA levels over 90%. Gene integration at the position downstream the stop codon can also reduce the OCH1 mRNA levels. However, gene integration at the position upstream the stop codon significantly increase the OCH1 mRNA levels. This result is similar to the observations of lacZ mRNA regulation in example 5.

Example 7

Protein Glycosylation in OCH1 Suppression Strain

Mammalian cells and yeast have the same N-glycosylation initiation step and modification process in endoplasmic reticulum. Precursor oligosaccharide Glc$_3$Man$_9$GlcNAc$_2$ of N-glycosylation is linked to Asn residues in the conserved sequence of nascent peptide chain Asn-X-Thr/Ser (X is an arbitrary amino acid other than Pro) while the nascent peptide chain is synthesized in endoplasmic reticulum, and then the sugar chains of the protein are processed to form Man$_8$GlcNAc$_2$ sugar chain structure under the action of glucosidase I and II glycosidase, and followed by transporting the protein with the sugar chain to Golgi apparatus. However, in mammalian cells and yeast Golgi apparatus, further modification and processing of the protein sugar chains will be significantly different. In Golgi apparatus of mammalian cells, the sugar chain of the protein is gradually processed to form a hybrid and complex type of sugar chain structure under the action of a series of mannosidase and glycosyltransferase; while in Golgi apparatus of *Pichia pastoris*, the sugar chain of the protein firstly accepted an α-1,6-mannose to form Man$_9$GlcNAc$_2$ sugar chain structure under the action of α-1,6-mannose transferase (Ochlp) encoded by OCH1 gene, and then mannose is continually added under the action of various mannose transferase (tens up to hundreds of mannose), and finally hyper-mannose type of sugar chain structure is formed and excessive glycosylating modification of protein is formed. Therefore, unlike mammalian cells, Ochlp is the first and most critical enzyme in yeast to form high mannosylation modification on proteins, and disruption of OCH1 gene is expected to block hyper-mannosylation modification on proteins in *Pichia pastoris* (Kornfeld, R. & Kornfeld, S. Assembly of asparagine-linked oligosaccharides. Annu. Rev. Biochem. 54, 631-664, 1985).

In order to block hyper-mannosylation modification, tremendous work had been conducted to knock-out genomic OCH1 in yeast. However, the efficiency of homologous gene targeting to disrupt encoding region of OCH1 gene and functions thereof is extremely low. In the present invention, gene integration at 5'OCH1 regulatory region is applied to block Ochlp-initiated hyper-mannosylation modification on proteins.

Codon optimized mouse interleukin-22 (mIL-22, DNA sequence of mouse IL-22 mature peptide containing his-tag with optimized codon for yeast is shown in SEQ ID NO: 129) was synthesized by Generay and used as a template for PCR amplification with primer pair of MIL22 F (SEQ ID NO: 124)/R (SEQ ID NO: 125). The PCR product was digested with XhoI and NotI restriction enzymes and cloned into the XhoI/NotI sites in pPICZα (Invitrogen) to yield mIL-22 expression vector, which can express and secret mIL-22 with his-tag. This expression vector was linearized with the restriction enzyme Sac I and electroporated into GS115 and och1(-1/+1) strains. Transformed cells were grown on YPD plate supplemented with Zeocin at 100 mg/L. The linearized vectors were integrated at AOX1 locus by single cross (roll-in) recombination as described by manufacturer (Invitrogen).

The transformed cells were grown in 5 ml YPD medium at 30° C. and 225 rpm shaking for 24 hours. Cells were pelleted by centrifugation at 3000 g for 5 minutes and resuspended in 5 ml BMGY medium to culture for 24 hours at 30° C. and 225 rpm shaking. Then cells were pelleted by centrifugation at 3000 g for 5 minutes and resuspended in 5 ml BMMY medium at 30° C. and 225 rpm to induce mIL-22 expression. Induction was maintained for another 72 hours by spiking the cultures twice daily with 50 μl of 100% methanol (1% final concentration). Subsequently, the cultures were harvested by centrifugation (3000 g for 10 minutes) and the supernatants were frozen at -20° C. until further use.

The his-tagged mIL-22 protein was purified from the supernatants by Ni-affinity chromatography following the manufacturer's instructions (Jingsirui biotech Ltd., Nanjing, China).

The glycans were released and separated from His-tagged mIL-22 protein by treatment of N-glycosidase F (PNGaseF) (New England Biolabs, Beverly, Mass.) using a previously reported method (Gregg J M (2010) *Pichia* Protocols, Second edition. Totowa, N.J.: Humanna Press).

Molecular mass of the glycans was determined using an Ultraflex MALDI-TOF (bruker daltonics, Bremen, Germany) mass spectrometer according to the manufacturer's instructions.

Figure 15A:
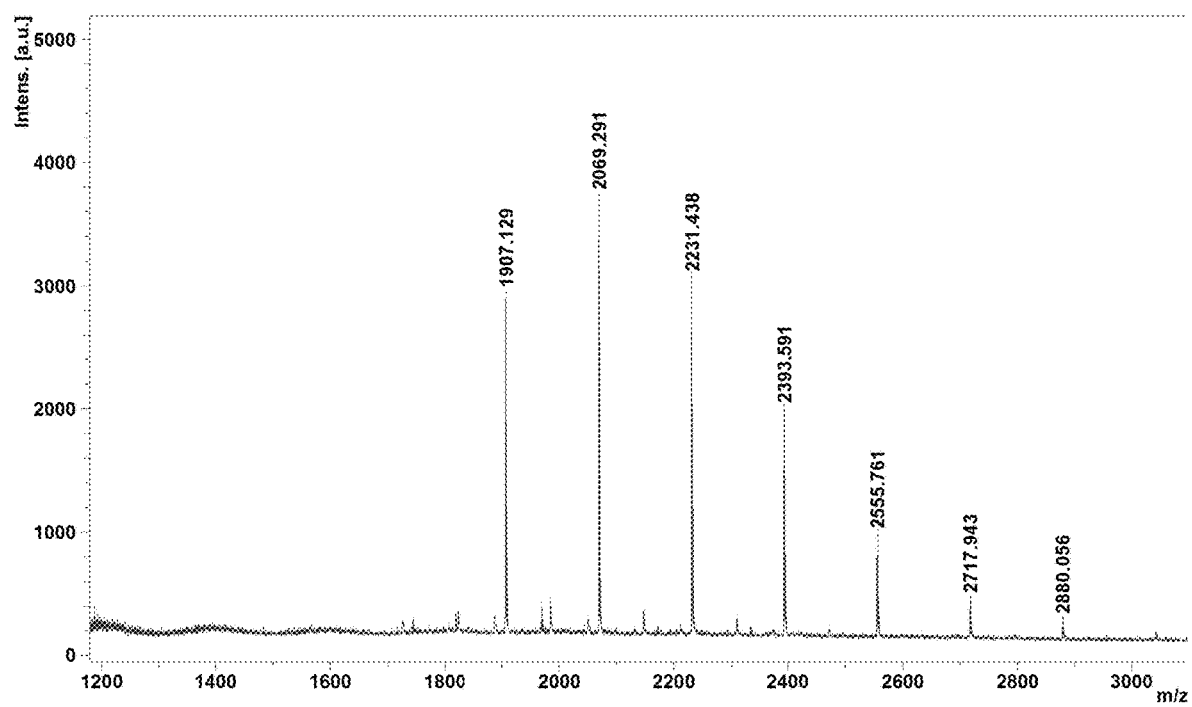
Figure 15B:
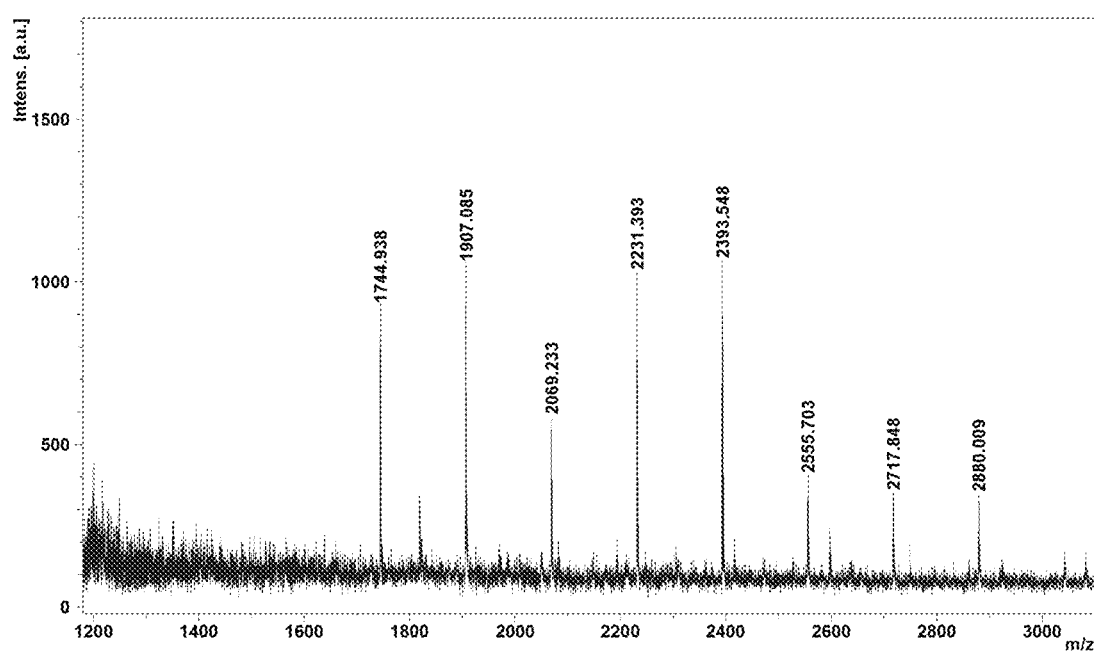

FIG. 15A shows mass spectrum of N-glycans released from mIL-22 in GS115 strain. It shows dominant hypermannosyl N-glycan, Man$_{9-15}$GlcNAc$_2$ (m/z: 1907, 2069, 2231, 2393, 2555, 2717, 2880), indicating that Ochlp initiated hyper-mannosylation modification on Man$_8$GlcNAc$_2$. FIG. 15B shows mass spectrum of N-glycans released from mIL-22 in och1(-1/+1) strain. It shows dominant hypermannosyl N-glycan, Man$_{8-15}$GlcNAc$_2$(m/z: 1744, 1907, 2069, 2231, 2393, 2555, 2717, 2880), wherein the hypermannosyl N-glycan may be formed under the action of other mannosyltransferase. Formation of Man$_8$GlcNAc$_2$ (m/z: 1744) indicates that gene integration upstream of encoding region of OCH1 can efficiently block Ochlp-initiated hypermannosyl modification (Choi, et al. (2003) Proc Natl Acad Sci USA 100: 5022-5027).

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A nucleotide construct for regulating a gene via a homologous recombination, comprising the following structure:

5'-A-B-C-3', wherein A is a 5' homologous sequence, B is an exogenous DNA that causes the gene to be regulated, and C is a 3' homologous sequence;

the nucleotide construct is configured so as to direct the exogenous DNA to a locus of a genome that contains the gene to be regulated;

the 5' homologous sequence and the 3' homologous sequence allow recombination sites of the nucleotide construct to be located between the first nucleotide of the start codon of the gene to be regulated and the $110^{th}$ nucleotide upstream from the first nucleotide of the start codon of the gene to be regulated, or the 5' and 3' homologous sequences allow the recombination sites of the nucleotide construct to be located between the first nucleotide upstream from the first nucleotide of the stop codon of the gene to be regulated and the third or the $204^{th}$ nucleotides downstream from the first nucleotide of the stop codon of the gene to be regulated;

the recombination sites include a 5' recombination site and a 3' recombination site;

the 5' homologous sequence is a sequence homologous to the 5' recombination site;

the 3' homologous sequence is a sequence homologous to the 3' recombination site, and transcription of the gene to be regulated is modulated by the exogenous DNA.

2. The nucleotide construct of claim 1, wherein the recombination sites are separated by 0-20 nucleotides.

3. The nucleotide construct of claim 2, wherein the recombination sites are separated by 0-5 nucleotides.

4. The nucleotide construct of claim 3, wherein the recombination sites are separated by 0 nucleotide.

5. The nucleotide construct of claim 1, wherein the gene to be regulated has a recombination efficiency of <3%, the recombination efficiency is efficiency of homologous recombination gene targeting.

6. The nucleotide construct of claim 5, wherein the gene to be regulated has a recombination efficiency of <1%.

7. The nucleotide construct of claim 5, wherein the gene to be regulated is OCH1 or ADE1 gene.

8. The nucleotide construct of claim 1, wherein the 5' homologous sequence and the 3' homologous sequence allow the recombination sites of the nucleotide construct to be located between the first nucleotide of the start codon of the gene and the $110^{th}$ nucleotide upstream from the first nucleotide of the start codon of the gene.

9. A host cell comprising the nucleotide construct of claim 1.

10. The host cell of claim 9, wherein the host cell is a yeast cell.

11. A method for regulating expression of a gene via a homologous recombination, comprising:
a) constructing the nucleotide construct of claim 1; and
b) introducing the nucleotide construct constructed in step a) into a cell, thereby integrating the nucleotide construct into the gene to be regulated via the homogeneous recombination.

12. The method of claim 11, wherein the gene to be regulated has a recombination efficiency of <3%, the recombination efficiency is efficiency of homologous recombination gene targeting.

13. The method of claim 12, wherein the gene to be regulated has a recombination efficiency of <1%.

14. A method for engineering a strain, comprising:
a) constructing the nucleotide construct of claim 1; and
b) introducing the nucleotide construct constructed in step a) into the strain to be engineered.

15. A method for producing a recombinant protein, comprising:
a) constructing the nucleotide construct of claim 1;
b) introducing the nucleotide construct constructed in step a) into a strain to be engineered; and
c) culturing the strain obtained in step b) to produce the recombinant protein.

16. A method for producing a metabolite,
a) constructing the nucleotide construct of claim 1;
b) introducing the nucleotide construct constructed in step a) into a strain to be engineered; and
c) culturing the strain obtained in step b) to produce the metabolite.

17. A method for conducting a biocatalytic reaction, comprising:
a) constructing the nucleotide construct of claim 1;
b) introducing the nucleotide construct constructed in step a) into a strain to be engineered; and
c) conducting the biocatalytic reaction with a culture of the strain obtained in step b).

* * * * *